US010347108B2

(12) United States Patent
Yan et al.

(10) Patent No.: US 10,347,108 B2
(45) Date of Patent: Jul. 9, 2019

(54) MONITORING USER ACTIVITY USING WEARABLE MOTION SENSING DEVICE

(71) Applicant: City University of Hong Kong, Kowloon (HK)

(72) Inventors: Hong Yan, Kowloon (HK); Leanne Lai Hang Chan, Kowloon (HK); Hung Chim, Kowloon (HK); Hong Yan Ching, Quarry Bay (HK); Chi Kuen Choi, Tin Shui Wai (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 30 days.

(21) Appl. No.: 14/598,949

(22) Filed: Jan. 16, 2015

(65) Prior Publication Data

US 2016/0210838 A1 Jul. 21, 2016

(51) Int. Cl.
*G08B 21/04* (2006.01)
*G08B 25/01* (2006.01)
(Continued)

(52) U.S. Cl.
CPC ....... *G08B 21/0446* (2013.01); *G08B 21/043* (2013.01); *G08B 25/001* (2013.01);
(Continued)

(58) Field of Classification Search
CPC ...... G08B 25/016; G08B 25/10; G08B 21/02; G08B 21/06; G08B 21/0461;
(Continued)

(56) References Cited

U.S. PATENT DOCUMENTS 8,868,616 B1* 10/2014 Otto ................... G06F 19/3418
378/19
2005/0075067 A1* 4/2005 Lawson ............. A61B 5/02055
455/1
(Continued)

FOREIGN PATENT DOCUMENTS

| WO | 2014052929 | 4/2014 |
| WO | 2014055240 | 4/2014 |
| WO | 2014059390 | 4/2014 |

OTHER PUBLICATIONS

Roving Networks, "Bluetooth Data Module Command Reference & Advanced Information User's Guide," Mar. 22, 2013, http://ww1.microchip.com/downloads/en/DeviceDoc/bluetooth_cr_UG-v1.0r.pdf. Last Accessed Apr. 8, 2015, 83 pgs.
(Continued)

Primary Examiner — Joseph H Feild
Assistant Examiner — Sharmin Akhter
(74) Attorney, Agent, or Firm — Amin, Turocy & Watson, LLP

(57) ABSTRACT

Facilitation of monitoring and analysis of user motion is performed to facilitate detecting when a user has fallen. A device can comprise a housing configured to attach to a body part of a human, a sensor module configured to capture motion data corresponding to motion of an object to which the device is attached, and a communication module configured to communicatively couple the sensor module to another device and transmit the motion data to the other device, wherein the motion data is configured to be analyzed by the other device to determine a type of the motion of the object, and in response to a determination that the type of motion is a falling motion, the other device is configured to activate a notification mechanism to notify an entity that the human has fallen.

27 Claims, 11 Drawing Sheets

(51) Int. Cl.
  *G08B 25/00* (2006.01)
  *G16H 40/63* (2018.01)
  *G16H 40/67* (2018.01)
(52) U.S. Cl.
  CPC ........... *G08B 25/016* (2013.01); *G16H 40/63* (2018.01); *G16H 40/67* (2018.01)
(58) Field of Classification Search
  CPC ......... G06F 17/30292; G06F 17/30289; G06F 17/30339; H04M 11/04; H04M 2242/04; H04M 3/5116
  USPC ................. 340/539.11–539.18, 573.1–573.4; 707/802–805; 379/37–40; 600/301
  See application file for complete search history.

(56) References Cited

U.S. PATENT DOCUMENTS

| | | | |
|---|---|---|---|
| 2006/0214806 A1* | 9/2006 | Clifford ................ | A61B 5/1117 340/573.1 |
| 2011/0066383 A1* | 3/2011 | Jangle ................... | A61B 5/1116 702/19 |
| 2012/0242501 A1* | 9/2012 | Tran ...................... | A61B 5/0024 340/870.02 |
| 2012/0314901 A1* | 12/2012 | Hanson ................. | A61B 5/0077 382/103 |
| 2013/0065569 A1* | 3/2013 | Leipzig .................. | G06F 9/453 455/416 |
| 2014/0065587 A1 | 3/2014 | Liebhart | |
| 2014/0066000 A1* | 3/2014 | Butler ............... | H04M 1/72538 455/404.2 |
| 2014/0067494 A1 | 3/2014 | Squires | |
| 2014/0077946 A1 | 3/2014 | Tran | |
| 2014/0184422 A1* | 7/2014 | Mensinger ........... | A61B 5/0004 340/870.02 |
| 2014/0266691 A1* | 9/2014 | McKinley ............. | G08B 25/016 340/539.11 |
| 2014/0266705 A1* | 9/2014 | McKinley ............. | G08B 25/10 340/539.13 |
| 2014/0375461 A1* | 12/2014 | Richardson ........ | G08B 21/0446 340/573.7 |
| 2015/0269827 A1* | 9/2015 | Hopkins ................. | H04W 4/90 340/539.12 |
| 2016/0038061 A1* | 2/2016 | Kechichian ........... | A61B 5/4035 600/301 |
| 2016/0275771 A1* | 9/2016 | Visweswara ......... | A61B 5/6822 |

OTHER PUBLICATIONS

J. Champion, "ZedGraph," Jan. 1, 2005, http://zedgraph.sourceforge.net/samples.html. Last Accessed Apr. 8, 2015, 1 pgs.
MikroElectronika, "Pic Real Time Clock—4 Methods for a Precision Time Clock," Apr. 16, 2007, http://www.mikroe.com/forum/viewtopic.php?t=10057. Last Accessed Apr. 8, 2015, 10 pgs.
D. Ibrahim, "SD Card Projects using the Pic Microcontroller", Amsterdam: Elsevier, 2009, 45 pgs.
Jimmy Liu, "[Raspberry Pi] Read MPU6050 gyroscope data use WiringPi libraries," Apr. 26, 2013, http://jimmyeestudio.blogspot.hk/2013/04/raspberry-pi-read-mpu6050-use-wiringpi.html. Last Accessed Apr. 8, 2015, 4 pgs.
X.-i. Technologies, "x-IMU Product Specification," Dec. 31, 2012, http://www.x-io.co.uk/products/x-imu. Last Accessed Apr. 8, 2015, 2 pgs.
Wireless Physiological Monitoring, "BioRadio—Wireless Motion Sensor," Jan. 1, 2014, http://glneurotech.com/bioradio/physiological-signal-monitoring/wireless-motion-sensor/. Last Accessed Apr. 8, 2015, 3 pgs.
"Safe@home System Detects Falls, Calls for Help," Feb. 3, 2014, http://www.medgadget.com/2014/02/safehome-system-detects-falls-calls-for-help.html. Last Accessed Apr. 8, 2015, 4 pgs.
A. Sadanandan, "MATLAB—CSVIMPORT," Apr. 6, 2009, http://www.mathworks.com/matlabcentral/fileexchange/23573-csvimport. Last Accessed Apr. 8, 2015, 4 pgs.
MathWorks, "Documentation Center—importdata," Jan. 1, 2013, http://www.mathworks.com/help/matlab/ref/importdata.html. Last Accessed Oct. 15, 2014, 6 pgs.
Steven W. Smith, The Scientist and Engineer's Guide to Digital Signal Processing, Second Edition, California : California Technical Pub, 1997, 688 pgs.
SensibilityTestbed, "Accelerometer Sensor Data Processing," Jan. 1, 2013, http://seattlesensor.wordpress.com/2013/01/01/accelerometer-sensor-data-processing/. Last Accessed Apr. 8, 2015, 6 pgs.
Google, "Google Tech Talk—Sensor Fusion on Android Devices: A Revolution in Motion Processing," Feb. 8, 2010, https://www.youtube.com/watch?v=C7JQ7Rpwn2k. Last Accessed Apr. 8, 2015 3 pgs.
E. Grant, "Finding the velocity from displacement," Nov. 19, 2011, http://www.mathworks.com/matlabcentral/answers/21700-finding-the-velocity-from-displacement. Last Accessed Apr. 8, 2015, 4 pgs.
New Tech Articles, "From where Internet comes? How It works?," Mar. 24, 2013, http://newtecharticles.com/from-where-internet-comes-how-internet-works/. Last Accessed Apr. 8, 2015, 8 pgs.
Design News Staff, "Combo Sensor Combines Six Functions," Dec. 24, 2010, http://www.designnews.com/document.asp?doc_id=229881&dfpPParams=ind_184,aid_229881&dfpLayout=article. Last Accessed Apr. 8, 2015, 5 pgs.
Digi-key, "STMicroelectronics L3G4200D is an ultra-stable three-axis digital output gyroscope," Dec. 1, 2010, http://www.digikey.com/product-highlights/us/en/stmicroelectronics-l3g4200d-gyroscopes/682. Last Accessed Apr. 8, 2015, 1 pg.
T. U. o. Waikato, "WEKA Manual for Version 3-7-8," Jan. 21, 2013, http://statweb.stanford.edu/~lpekelis/13_datafest_cart/WekaManual-3-7-8.pdf. Last Accessed Apr. 8, 2015, 327 pgs.
J. Borenstein, Heuristic Reduction of Gyro Drift in IMU-based Personnel Tracking Systems, Michigan: The University of Michigan, 2009, 11 pgs.
C. Y. Yong, "Distance: A Moderator between Walking Activity and Pattern Classification," Universiti Teknologi Malaysia, Malaysia, 2012, 6 pgs.
P. C. Pak-kwong, "Zhongbo Guang Rubric: fell to his death after a traffic accident death toll", Dec. 8, 2013, http://paper.wenweipo.com/2013/12/08/SP1312080036.htm. Last Accessed Apr. 8, 2015, 2 pgs.
"Chinese elderly population this year will break the 200 million annual growth rate of ten million," Oct. 13, 2013, http://hk.crntt.com/doc/1027/9/3/8/102793812.html?coluid=50&kindid=1072&docid=102793812. Last Accessed Apr. 20, 2015, 4 pgs.
Beijing elderly fall accident mortality rate of 3.79% as the fifth leading cause of death, Jan. 17, 2014, http://news.cnr.cn/native/city/201401/t20140117_514680635.shtml. Last Accessed Apr. 8, 2015, 4 pgs.
Freescale Semiconductor, "Xtrinsic MMA8451Q 3-Axis, 14-bit/8-bit Digital Accelerometer Datasheet," Oct. 1, 2013, http://cache.freescale.com/files/sensors/doc/data_sheet/MMA8451Q.pdf?fasp=1&Parent_nodeId=1280942466187701001159&Parent_pageType=product. Last Accessed Apr. 8, 2015, 55 pgs.
K. Tuck, "Motion and Freefall Detection Using the MMA8451Q," Oct. 1, 2011, http://cache.freescale.com/files/sensors/doc/app_note/AN4070.pdf. Last Accessed Apr. 8, 2015, 13 pgs.
Sherrill, et al. "Journal of NeuroEngineering and Rehabilitation," Feb. 1, 2005, http://www.jneuroengrehab.com/content/2/1/16/figure/F2. Last Accessed Apr. 8, 2015, 1 pg.
Mitsuaki Ishii, "Analysis of Freezing of Gait Using the Tri-Axial Accelerometer in Parkinson's Disease," Mar. 1, 2010, http://archives.bukkyo-u.ac.jp/rp-contents/HO/0004/HO00040L011.pdf. Last Accessed Feb. 23, 2014, 9 pgs.
C. S. Lee, "Bluetooth Security Protocol Analysis and Improvements," May 1, 2006, http://citeseerx.ist.psu.edu/viewdoc/download?doi=10.1.1.122.3116&rep=rep1&type=pdf. Last Accessed Apr. 8, 2015, 60 pgs.
K. Tuck, "Data Manipulation and Basic Settings of the MMA8451Q," Jan. 3, 2012, http://cache.freescale.com/files/sensors/doc/app_note/AN4076.pdf. last Accessed Apr. 8, 2015, 23 pgs.

(56) References Cited

OTHER PUBLICATIONS

InvenSense, "MPU-6050 Product Specification Revision 3.4," Aug. 19, 2013, http://www.invensense.com/mems/gyro/documents/PS-MPU-6000A-00v3.4.pdf. Last Accessed Apr. 8, 2015, 52 pgs.

InvenSense, "MPU-6050 Register Map and Descriptions Revision 4.0," Mar. 9, 2013, http://invensense.com/mems/gyro/documents/RM-MPU-6000A.pdf. Last Accessed Apr. 8, 2015, 47 pgs.

Microchip, "PIC32MX5XX/6XX/7XX Family Data Sheet," Apr. 22, 2013, http://ww1.microchip.com/downloads/en/DeviceDoc/61156H.pdf. Last Accessed Oct. 1, 2013, 448 pgs.

Roving Networks, "RN-41 Datasheet," Apr. 8, 2009, http://medialappi.net/lab/download/datasheets/RN-41.pdf. Last Accessed Apr. 8, 2015, 7 pgs.

* cited by examiner

MONITORING USER ACTIVITY USING WEARABLE MOTION SENSING DEVICE

TECHNICAL FIELD

This application generally relates to a wearable motion sensing device and system that facilitate monitoring user activity.

BACKGROUND

Many countries are facing upsurge in the aging population. For example, in China, there are currently over 200 million elderly men and women. This number is expected to grow at the rate of 10 million per year. Health care service providers have found it challenging to keep up with the high demand for elderly health care services. Among the various health care services received by elderly patients, rehabilitation from accidents has been found to be one of the most common. Even more noteworthy, a recent study conducted on the elderly population in Beijing found accidental falling to be one of the top five fatality causes, concluding that about 100,000 people were killed in Beijing in 2013 as a result of accidental falling. A similar study conducted in Hong Kong, declared accidental falling as the second highest cause of fatalities in 2013, finding accidental falling to be the cause of death for about 420,000 men and women. One of the main contributors to fatalities based on accidental falling is untimely rescue. Accordingly, there is a strong need for mechanisms to reduce the amount of time associated with finding and attending to victims of accidental falling after the occurrence of an accident.

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
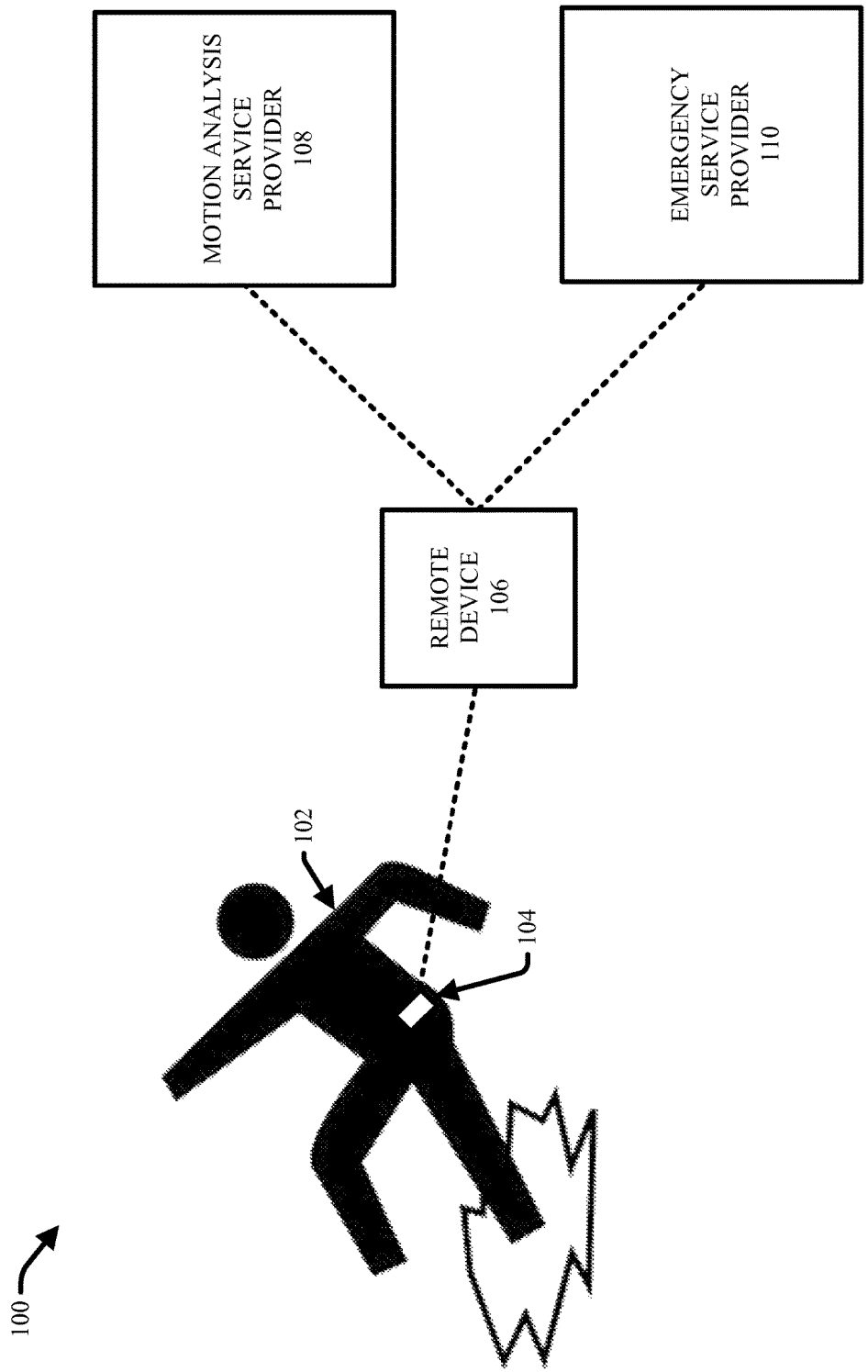
FIG. 1 illustrates an example system that facilitates selecting monitoring and analyzing user motion in association with provision of various motion based services in accordance with various aspects and embodiments described herein.

The subject application is described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and components are shown in block diagram form in order to facilitate describing the various embodiments.

By way of introduction, the subject matter described in this disclosure relates to a wearable motion sensing device and system that facilitate monitoring user activity. In an aspect, a small motion sensing device is provided that can be worn by a user (e.g., attached to clothing, a belt, a body part, etc.) and configured to capture motion data corresponding to motion of the user. For example, the motion sensing device can be worn by the user throughout the user's day and capture information regarding the user's movement/motion throughout the day. In another example, the motion sensing device can be worn for a specific period of time or physical performance activity, (e.g., throughout the night as the user sleeps or while the user runs a race), and capture specific motion information regarding the period of time or physical performance activity.

The disclosed motion sensing device includes a sensor module that includes one or more sensors or sensing devices configured to capture motion data. These can include can but are not limited to, an accelerometer, a gyroscope, a magnetometer, and/or an inertial-measurement unit (IMU). In an aspect, the motion sensing device is configured to capture motion information indicating acceleration and rotation of the motion sensing device. The motion sensing device further includes a mechanism for storing the captured motion and/or sending the captured motion data to another device for processing/analysis. In an aspect, the motion sensing device can include a microprocessor that facilitates onboard analysis of captured motion data.

Captured information regarding a user's motion can be analyzed to identify various characteristics about the user's motion. In an aspect, captured motion data is analyzed using pattern recognition analysis to identify various patterns in the motion data that correspond to known movements or motions, such as walking, running, jumping, rolling, walking stairs, falling, standing up, laying or sitting down, etc. Machine learning techniques can be employed in association with pattern analysis to enhance accuracy of pattern based motion determinations. Identified movements, as well as determinations of duration and intensity of the movements, can further be correlated to user activity levels, user activity patterns, user health characteristics (e.g., calories burned by the user), user sleep patterns, and various other aspects related to user movement.

In an exemplary embodiment, motion data is captured by a motion sensing device worn by or otherwise attached to a user and analyzed in real-time to facilitate real-time monitoring of a user's motion and movement patterns. For example, the disclosed motion sensing device can transmit motion data to another device via a wireless network (e.g., personal area network (PAN), a local area network (LAN), a wide area network (WAN), etc.), using various wireless communication protocol (e.g., Bluetooth™, Wi-Fi, ZigBee, etc.) as it captured and/or in response to capture thereof. The other device can then be configured to analyze the motion data as it is received. According to this embodiment, real-time monitoring of user motion/movement is employed to detect when a user wearing the motion sensing device has fallen. In particular, a recent study conducted in Beijing has shown that accidental falling is the fifth leading cause of home injury deaths for the elderly. A main reason for serious injury or death due to accidental falling is untimely rescue. Thus according to an embodiment, a motion sensing device and system is provided that is designed to capture and analyze motion patterns corresponding to falling down. When falling down is detected without further motion, help can be called or notified automatically by the sensing device or a remote device configured to interact with the sensing device.

In an aspect, a motion sensing device worn by a user is configured to capture motion data over the course of wear and transmit the motion data to another device over a wireless network as it is captured. For example, the other device can include a mobile device employed by the user (e.g., the user's cellular phone, tablet personal computer). In another example, the other device can include a stationary computing device provided in the user's home. In another example, the other device can include a network node configured to communicate the motion data to a remote monitoring system. Upon receipt of the motion data, the receiving device can be configured to process the motion data to identify patterns in the motion data. When a pattern in the motion data is detected that correlates to a falling motion, the other device can activate a notification mechanism to notify another user or emergency personnel that the user has fallen. In an aspect, the notification mechanism can provide for determining at least the location of the fallen user.

For example, the other device can sound an alarm that can be heard by surrounding people to indicate the user is in distress and needs help. In another, example, the other device can send an electronic notification message to emergency services (e.g., that can be received at mobile devices of emergency personnel, and/or a central server device employed by the emergency services). In an aspect, the electronic message (e.g., a notification message, an email, a short messaging service (SMS) text message, an instant messaging service message, etc.) can include information identifying the location of the user and/or an identity of the user and indicate that the user has fallen. In another aspect, where the other device is a phone, the other device can automatically initiate a phone call to emergency services or another designated entity. The other device can also activate a speaker of the phone so that the fallen user can communicate with the recipient caller without having to move to access the other device.

In another aspect, the motion sensing device can include onboard processing. According to this aspect, the motion sensing device can be configured to specifically determine when captured motion data corresponds to a falling motion. In response to determination that the user has fallen based on detection of the falling motion, the motion sensing device can activate a transmitter of the motion sensing device and emit a distress signal. The distress signal can be configured for interpretation by another device. For example, another device can be configured to listen for the distress signal. Upon detection of the distress signal, the other device can activate a notification mechanism, (e.g., those listed above), to notify another user or emergency personnel that the user has fallen. In another example, in response to determination that the user has fallen based on detection of the falling motion, the motion sensing device itself can include and sound an alarm. Still in yet another example, the motion sensing device itself can include functionality to send an electronic message or initiate a phone call.

In addition to monitoring and reporting a falling incident of a user wearing the disclosed sensing device, by analyzing collected motion data for a user, health reports based on the user's motion can be generated, sleep patterns can be evaluated and diagnosed, and even calories burned throughout the day or during exercise could be produced to improve the users fitness. Further, the subject sensing device can be employed to monitor motion of other objects or things aside from humans. For example, in logistic, sometimes items are labeled with a 'handle with care' sign to ask the crew to take extra caution in transporting the items. A motion sensing device can be attached to such an item and gather and store motion data for the item throughout transport. Later, the data gathered by the sensor can be analyzed to determine if the item was mishandled (e.g., allowed to drop or fall).

In an aspect, a device is provided that includes a housing configured to attach to a body part of a human, a sensor module configured to capture motion data corresponding to motion of an object to which the device is attached, and a communication module configured to communicatively couple the sensor module to another device and transmit the motion data to the other device, wherein the motion data is configured to be analyzed by the other device to determine a type of the motion of the object, and in response to a determination that the type of motion is a falling motion, the other device is configured to activate a notification mechanism to notify an entity that the human has fallen.

In another aspect, a device is provided that includes a housing configured to attach to a human and a sensor module configured to capture motion data corresponding to motion of the human to which the device is attached. The device further includes a memory that stores executable components and a processor that executes or facilitates execution of the executable components, including at least an analysis component configured to analyze the motion data as it is captured to determine a type of the motion and a transmission component configured to transmit a distress signal that indicates the human to which the device is attached has fallen in response to a determination that the type of motion is a falling motion.

In another aspect, a device is disclosed that includes a memory that stores executable components, and a processor that executes or facilitates execution of the executable components, including a reception component configured to receive motion data captured by a motion detection device attached to a body part of a human, the motion data corresponding to motion of the human, an analysis component configured to analyze the motion data to determine a type of the motion, and a notification component configured to activate a notification mechanism to notify another entity that the human has fallen in response to a determination that the motion is a falling motion.

In yet another aspect, a method is provided that includes receiving, by a system comprising a processor, motion data captured by a motion detection device attached to a body part of a human, the motion data corresponding to motion of the human, analyzing, by the system, the motion data to determine a type of the motion, and activating, by the system, a notification mechanism to notify another entity that the human has fallen in response to a determination that the motion is a falling motion.

Further provided is a tangible computer-readable storage medium comprising computer-readable instructions that, in response to execution, cause an apparatus comprising a processor to perform various operations. These operation can include capturing, by a motion detection device comprising a processor, motion data corresponding to motion of a human to which the motion detection device is attached, analyzing, by the motion detection device, the motion data after capture to determine a type of the motion, and transmitting, by the motion detection device, a distress signal that indicates the human has fallen in response to a determination that the type of motion is a falling motion.

Referring now to the drawings, with reference initially to FIG. 1, presented is a diagram of an example system 100 that facilitates tracking and analyzing user motion patterns in accordance with various aspects and embodiments described herein. Aspects of systems, apparatuses or processes explained in this disclosure can constitute machine-executable components embodied within machine(s), e.g., embodied in one or more computer readable mediums (or media) associated with one or more machines. Such components, when executed by the one or more machines, e.g., computer(s), computing portable device(s), virtual machine(s), etc. can cause the machine(s) to perform the operations described.

System 100 includes a motion sensor device 104 being worn by a person/user 102, a remote device 106, motion sensor analysis service provider 108 and emergency service provider 100. Motion sensor device 104 can include a small, lightweight, portable device that can be easily worn or carried by a user. For example, motion sensor device 104 can include a battery bowered device that can be held in a user's clothing pocket, attached to a user's belt or other clothing garment, worn around a user's wrist, included in a user's shoe, etc. In an exemplary embodiment, motion sensor device 104 includes a rechargeable battery configured to facilitate all day wear and usage.

System 100 can also include one or more wireless networks to facilitate connection/communication between motion sensor device 104, remote device 106, motion sensor analysis service provider 108 and emergency service provider 100. These networks can include wired and wireless networks, including but not limited to, a cellular network, a wide area network (WAD, e.g., the Internet), a local area network (LAN), or a personal area network (PAN). For example, motion sensor device 104 can communicate with remote device 106 using a PAN (e.g., via short range radio communications). In another example, remote sensing device 104 and/or remote device 106 can communicate with motion sensor analysis service provider 108 and/or emergency service provider 100 (and vice versa) using virtually any desired wired or wireless technology, including, for example, cellular, Bluetooth™, Wi-Fi, ZigBee, etc. In some embodiments, one or more of motion sensor device 104, remote device 106, motion sensor analysis service provider 108 or emergency service provider 100 can include memory that stores computer executable components and a processor that executes the computer executable components stored in the memory, examples of which can be found with reference to FIG. 10.

Motion sensor device 104 can include a small, portable and lightweight electronic device configured to be worn or otherwise attach to a part of a human body (or other object) and capture information regarding motion of the human body (or other object). For example, motion sensor device 104 can be configured to clip onto an article of clothing, a belt, glasses, headband, or other accessory. In another example, motion sensor device 104 can be worn around a user's wrist or ankle or carried in the user's pocket. In an aspect, to facilitate detection of a falling motion of user 102, motion sensor device 104 is particularly configured to be worn at or near the user's waist or trunk.

Motion sensor device 104 can include a housing and various electronic components encased within the housing including at least a sensor module configured to capture motion data in response to motion of the motion sensor device 104 over a period of time (e.g., sampling period). When worn by user 102, the captured motion data directly corresponds to motion of the user 102. The sensor module of motion sensor device 104 can include various motion sensors including one or more of an accelerometer, a gyroscope, a magnetometer, and/or an IMU. Thus captured motion data can include information identifying acceleration, rotation/orientation, and/or velocity of the motion sensor device 104. Motion sensor device 104 can also include a timer to relate captured motion data as a function of time.

In an aspect, motion data captured by motion sensor device 104 is recorded in nonvolatile memory (e.g., a secure digital (SD) card) of the device 104. The recorded motion data can later be transferred to another device (e.g., via a direct wired connection or wireless connection), such as remote device 106, for processing thereof.

In another aspect, raw motion data captured by motion sensor device 104 can be communicated to another device or system, such as remote device 106, motion analysis service provider 108, and/or emergency service provider 100, in response to capture by the motion sensor device 104 (e.g., in real-time or near real-time). The other device or system can then process and analyze the raw motion data as it is received, (e.g., in real-time or near real-time as it is generate). For example, remote device 106 can include a mobile computing device such as a smartphone or tablet personal computer configured to receive raw motion data from motion sensor device 104 with which it is paired and process the captured motion data as it is received. In another example, motion analysis service provider 108 can include a networked service provider configured to receive motion data from motion sensor device 104 (e.g., either directly or relayed thereto via remote device 106), and process the raw motion data. According to this example, motion analysis service provider 108 can provide various network based services for a plurality of motion sensing devices and their affiliated users, such as real-time motion based analysis, report generation, and emergency services notification. Emergency service provider 100 can include a networked entity configured to provide emergency services to users. For example, emergency service provider 100 can include a call center that receives calls/messages for emergency services and deploys appropriate personnel (e.g., ambulance, medical caregivers, police, etc.) to the location of need.

In yet another aspect, motion data captured by motion sensor device 104 can be processed in full or in part by motion sensor device 104. The processed motion data and/or a response based on the processed motion data, such as triggering of an emergency response function or output of a report, can then be communicated to another device or system, (e.g., remote device 106, motion analysis service provider 108, and/or emergency service provider 100).

Processing of raw motion data can include pattern analysis to determine or infer types of motion represented by the motion data and/or characteristics associated with the types of motion. For example, using pattern recognition, patterns in the motion data can be correlated to know patterns for different types of motion, such as walking, running, jumping, rolling, walking stairs, and falling, standing up, laying or sitting down, etc. In an aspect, motion data can be processed in real-time to determine a type of motion of a user and to provide real-time analysis of the type of motion and responses based on the analysis (e.g., activation of emergency services in response to detection of a falling motion, provision of a notification to the wearer of motion sensor device 104 to become more or less active at a given point in time, etc.). In another embodiment, a user's motion and non-motion over a sampling period of a day, a week, etc. can be employed to study the user's activity patterns and determine health characteristics associated with the activity patterns. For example, based on user's motion and type of motion over the course of a 24 hour period, information can be discerned regarding amount of daily activity, amount of calories burned, amount of sleep, sleep restlessness, correlation of sleep and activity levels/patterns, etc.

In an exemplary embodiment, motion sensor device 104 is configured to facilitate detecting falling of user 102 and automatically contacting/notifying emergency services in response. In an aspect, motion sensor device 104 can communicate raw motion data to remote device 106 as it is captured (e.g., over a wireless network). In turn, remote device 106 can process the raw motion data to determine whether a falling motion has occurred or is occurring (e.g., using pattern recognition). For example, motion sensor device 104 can be paired with remote device 106 and communicate captured motion data to remote device 106 (e.g., a mobile device 102 owned by the user and located within proximity to the user 102) using short range radio waves (e.g., via Bluetooth™, near field communication (NFC), wireless fidelity (WiFi), etc.). Remote device 106 can then process the raw data as it is received. In response to detection of a falling motion, remote device 106 can then be configured to contact emergency service provider 100 to notify the emergency service provider 100 that the user 102 has fallen so that rescue protocol can be deployed to help the fallen user.

For example, remote device 106 can include a phone (e.g., a smartphone) configured to automatically initiate a phone call to emergency service provider 100 to allow user 102 to speak with personnel at emergency service provider 100 in response to a determination that user 102 has fallen. In another example, remote device 106 can send an electronic message (e.g., in a recorded audio format, in a text format, in a distress signal format, etc.) to emergency service provider 100. According to this example, remote device 106 can be configured to communicate with emergency service provider 100 via a wireless network (e.g., a cellular network, the Internet, etc.) using various known wireless communication protocol.

In an aspect, in association with contacting emergency service provider 100 in response to detection of falling of user 102, remote device 106 can provide information indicating a location and/or identity of the fallen user 102. For example, the remote device 106 be configured to determine its location at the time falling is detected (e.g., using a global positioning system (GPS) based locating mechanism, a triangulation based locating mechanism, a time-based locating mechanism, etc.), and include its location information in association with reporting the fallen user 102 to an emergency service provider 100 or other response system. Because remote device 106 will likely be within relatively close proximity of the fallen user, the location of the remote device 106 can provide a relatively accurate indication of where the fallen user is located. In another example, information identifying the user (e.g., the user's name and other information about the user) can be discerned (e.g., by remote device 106 or emergency service provider 100) via a known association of the user's identity with an identifier for the motion sensor device 104 and/or remote device 106 (e.g., a phone number). This identifier and/or a determination of the user's identity based on the identifier, can be provided to emergency service provider 100.

In another aspect, motion sensor device 104 can communicate raw motion data to remote device 106 as it is captured. In turn, remote device 106 can function as an intermediary network transfer device (e.g., a network node or access point) and relay captured motion data to motion analysis service provider 108. Motion analysis service provider 108 can include a networked service configured to receive and process motion data from one or more motion sensor devices 102. (Various features of motion service provider 108 are discussed in greater detail infra with respect to FIG. 6.) For example, motion sensor device 104 can transmit raw motion data to remote device 106 over a PAN using short range radio waves and remote device 106 can relay the raw motion data to motion analysis service provider 108 via a WAN. Upon receipt of the raw motion data, motion analysis service provider 108 can process the raw motion data to determine whether a falling motion has occurred or is occurring (e.g., using pattern recognition) for user 102. Upon detection that user 102 has fallen based on analysis of the raw motion data, motion analysis service provider can be configured to automatically contact and notify emergency service provider 100.

In yet another aspect, motion sensor device 104 can process raw captured motion data in real-time to detect a falling motion (e.g., using pattern recognition analysis). In response to detection of a falling motion, motion sensor device 104 can activate a transmitter of the motion sensor device 104 and output a distress signal or beacon that indicates user 102 has fallen. Remote device 106 can be configured to listen for this distress signal or beacon. In response to detection of the distress signal or beacon, remote device 106 can contact emergency service provider 100 or otherwise initiate an emergency response protocol. In another aspect, motion sensor device 104 can be configured to include capabilities to contact emergency service provider 100 directly (e.g., without employing remote device 106) in response to detection of falling of user 102. For example, motion sensor device 104 can transmit an electronic notification message to emergency service provider 100 that can be received and interpreted by emergency service provider 100. The electronic notification message can indicate that user 102 has fallen and facilitate determination of a location and/or identify of user 102.

It should be appreciated that the various components of system 100 can interact via various networks using various wireless communication technologies. In addition, processing of raw motion data captured by motion sensor device 104 can be provided in full or in part (in real-time or non-real time) at motion sensor device 104, remote device 106, motion analysis service provider 108 and/or emergency service provider 100. The various aspects, of motion sensor device 104, remote device 106, and motion analysis service provider 108 are respectively discussed in greater detail infra with respect to FIGS. 2-6.

Figure 2:
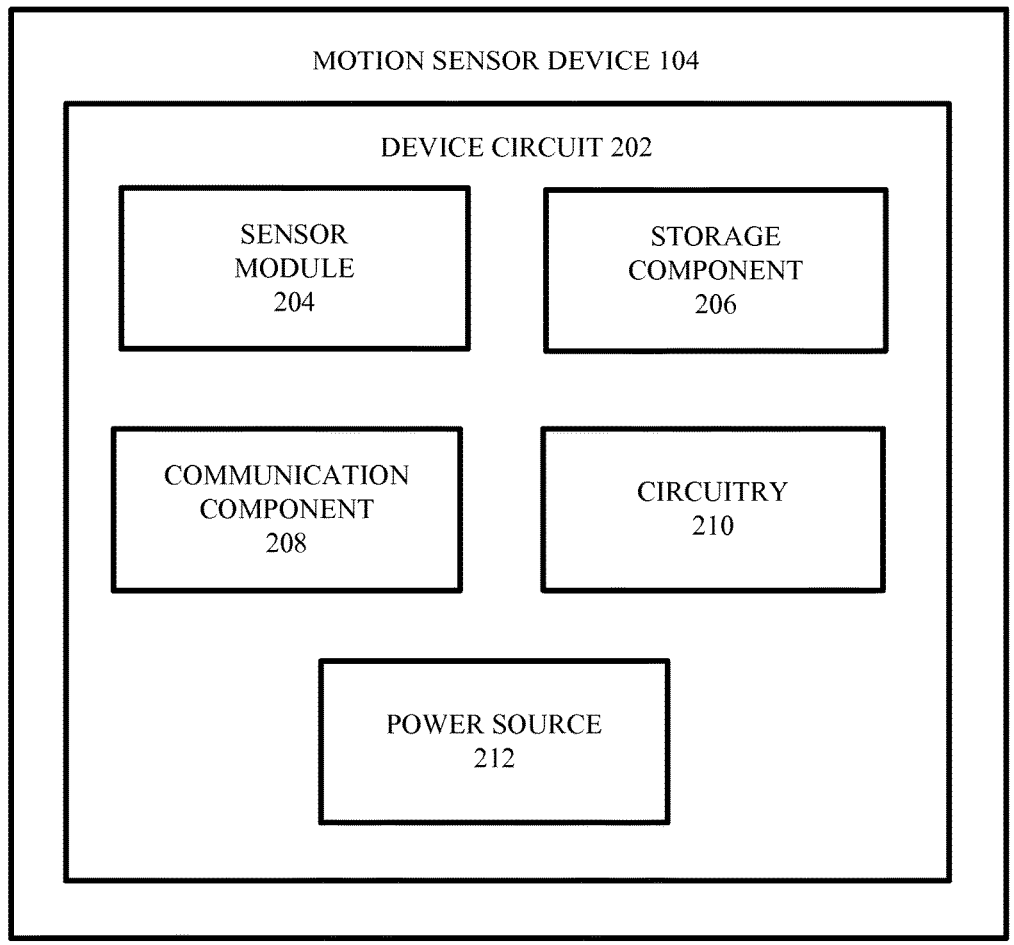
FIG. 2 presents an example motion sensor device in accordance with various aspects and embodiments described herein.

FIG. 2 presents an exemplary embodiment of motion sensor device 104 in accordance with aspects described herein. Repetitive description of like elements employed in respective embodiments of devices and systems described herein is omitted for sake of brevity.

Motion sensor device 104 includes a device circuit 202 provided within a housing. The material and configuration of the housing can vary. In an aspect, the housing facilitates attachment to a part of a human body or article of clothing. In another aspect, the housing can facilitate attachment to another object capable of movement or being moved by an external force (e.g., an animal, a box, a vehicle, etc.). Device circuit 202 includes sensor module 204, storage component 206, communication component 208, circuitry 210 and power source 212.

Sensor module 204 includes one or more sensors configured to capture motion data in response to motion of a subject (e.g., user 102 or another object) to which sensor device 104 is attached, including but not limited to, an accelerometer, a gyroscope, a magnetometer and/or an IMU. An accelerometer captures the acceleration it perceives in three axis (e.g., X-axis, Y-axis and Z-axis). The accelerations are usually expressed in terms of gravity (g) (1 g=9.81 ms$^{-2}$). Acceleration data can roughly facilitate estimation of a distance traveled by the device 104 and an orientation of the device. A gyroscope captures more accurate data regarding orientation of the device 104 and an IMU is a sensor that integrates an accelerometer and gyroscope. An IMU can be used to capture complementary information, such as tilting of the device 104 during motion, velocity of the device 104 and acceleration/deceleration of the device 104, which can be useful in motion pattern recognition.

In an aspect, sensor module 204 can also facilitate determining a location of the motion sensing device 104. For example, sensor module 204 can include a global positioning system (GPS) client to facilitate determining its GPS location at a time when motion data is captured and/or at a time when processed motion data indicates the user 102 wearing the motion sensor device 104 has fallen. The motion sensor device 104 can further report its location to remote device 106 and/or another device (e.g., emergency service provider) in association with reporting the captured motion data and/or information indicating the user 102 wearing the motion sensor device 104 has fallen.

In an aspect, to minimize cost, complexity and power consumption by motion sensor device 104, the sensor module 204 includes only an accelerometer configured to capture acceleration measurements of the motion sensing device 104 including static acceleration measurements or dynamic acceleration measurements. Static acceleration measurements report the sum of acceleration perceived in 3-axis format. For example, if a car is accelerating in the X-direction in 1 ms$^{-2}$ and the Z-direction is perpendicular to the ground, the output will be 1 ms$^{-2}$ in the X-direction and 9.81 ms$^{-2}$ in the Z-direction. Therefore, static accelerometer measurements can facilitate determination of an orientation of the device 104 in addition to acceleration of the device.

Activation of the sensor module 204 to accomplish sampling/capture of motion data can be controlled on motion sensor device 104 and/or via a remote device (e.g., remote device 106, motion analysis service provider 100, or another device with remote control capabilities). For example, a button or switch can be provided on motion sensing device that can allow the wearer to start and stop sampling. In an aspect, this switch can simply include a power button. For example, when motion sensor device is turned on it can continuously capture motion data. To stop sampling the user can merely turn the device off. In another example, sampling periods can be programmed/controlled at a remote device.

In an aspect, captured motion data is recorded at motion sensor device 104 by storage component 206. According to this aspect, captured motion data can be gathered by motion sensor device 104 for transfer to another device for processing at a later time. For example, storage component 206 can include a non-volatile memory component such as a resident non-volatile memory component that can be read out by another device connected to motion sensor device 104 (e.g., via a wired or wireless connection). In another example, storage component 206 can include a removable non-volatile memory component (e.g., an SD card). In some aspects, motion sensor device 10 is configured to record captured motion data into storage component 206 when at least one of: a remote device is not accessible for wireless communication of the data, a high sampling rate is required (data speed on SD card is faster than that on Bluetooth™) or a real-time response is not required.

In another aspect, motion sensor device 104 is configured to send captured motion data to another device for processing using communication component 208. For example, communication component 208 can include a transmitter or transceiver configured to wirelessly transmit raw motion data to another device (e.g., remote device 106, motion analysis service provider 108). Communication component 208 can support and employ various wireless communication technologies to transmit captured motion data to another device. For example, communication component 208 can employ short range radio transmissions configured for interception by another device within relatively close proximity to motion sensor device (e.g., from a few centimeters to about 50 meters). According to this example, communication component 208 can communicate with the other device using Bluetooth™, Wi-Fi, ZigBee, NFC, and the like. In another example, communication component 208 can be configured to employ various wide-range wireless communication protocols and/or communicate with remote systems/devices using a WAN.

In an aspect, communication component 208 is configured to transmit captured motion data to the other device in real-time (e.g., as it is captured) for processing by the other device in real-time (e.g., as it is received). For example, communication component 208 can send captured motion data to remote device 106, wherein remote device 106 is configured to determine a type of the motion of the user to which the motion sensor device 104 is attached as the motion data is received (e.g., using pattern recognition). In response to a determination that the type of motion is a falling motion, the remote device can activate a notification mechanism to notify another entity (e.g., another person/device, emergency service provider 100, etc.) that the user has fallen.

Circuitry 210, provides the necessary connections between the components of device circuit 202 for the operation of the device circuit. For example circuitry 230 facilitates the collection of signals generated by the sensor module 204. Circuitry 210 can further send detected signals/values to storage component 206 and/or communication component 208. Power source 212 can include any suitable power source (e.g. a battery, a capacitor, a solar power source, a wireless power source, a mechanical energy harvesting device, etc.) that can provide necessary power for the operation of the various component of the device circuit 202. In an aspect, the power source 212 can include a rechargeable power source.

Figure 3:
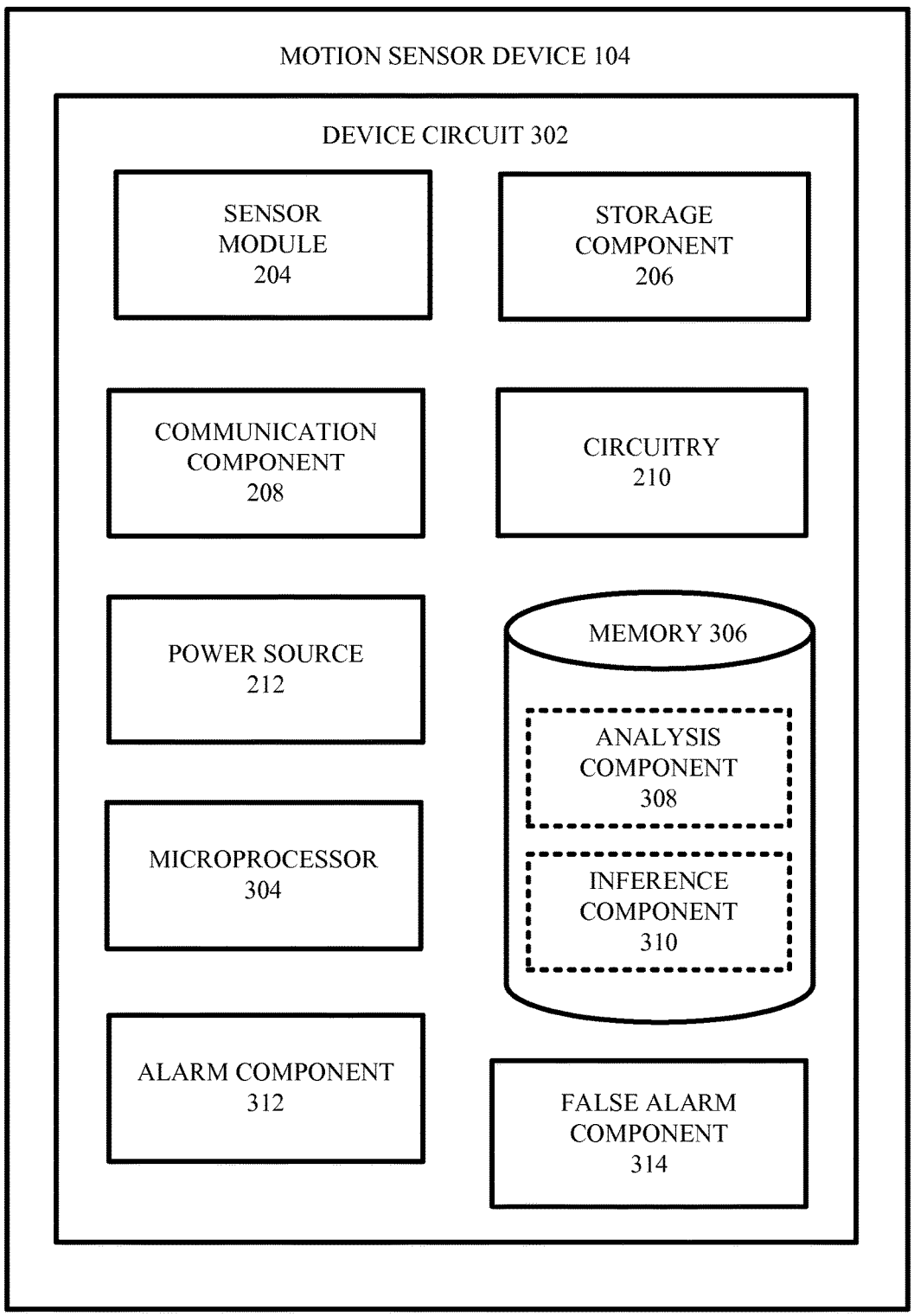
FIG. 3 presents another example motion sensor device in accordance with various aspects and embodiments described herein.

FIG. 3 presents another exemplary embodiment of motion sensor device 104 in accordance with aspects described herein. Motion sensor device 104 can include device circuit 302. Device circuit 302 can include one or more of the components of device circuit 202 with the addition of microprocessor 304, memory 306, alarm component 312 and false alarm component 314. Repetitive description of like elements employed in respective embodiments of devices and systems described herein is omitted for sake of brevity.

Device circuit 302 can include microprocessor 304 and memory 306 to provide for onboard processing of motion data captured by sensor module 204. In particular, memory 306 can store computer executable components, including analysis component 308 and inference component 310 and microprocessor 304 can be configured to execute or facilitates execution of the executable components.

Analysis component 308 is configured to analyze captured motion data to identify patterns in the motion data that correspond to various movements. In an aspect, analysis component 308 is particularly configured to detect signals in the motion data that correspond to a falling motion. According to this aspect, in response to detection of a falling motion, analysis component 308 can direct communication component 208 to transmit a distress signal for reception by another device (e.g., remote device 106 or emergency service provider 100) that indicates the user to which motion sensor device 104 is attached has fallen. The distress signal can also include information indicating the identity of the fallen user and/or a location of the fallen user.

According to this embodiment, rather than continuously transmitting raw motion data to another device for processing in real-time, communication component 208 can remain inactive (e.g., turned off) unless a determination is made that the user has fallen, thus conserving power. The communication component 208 can then activate its transmitter to send the distress signal when necessary. Raw motion data can also be stored by storage component 206 for future retrieval and analysis (e.g., by another device or analysis component 308).

In some aspects, in response to detection of a falling signal, analysis component 308 can also direct alarm component 312 to signal/sound an alarm 312 (e.g., an audible alarm, a visible alarm such as a blinking light, etc.). For example, alarm component 312 can include a speaker, horn, or buzzer configured to emit a loud siren that can be heard by surrounding people. According to this aspect, in addition to transmitting a distress signal, motion sensor device 104 can also notify surrounding good Samaritans that the user in distress. In addition, the alarm can serve to notify the user that emergency services have been contacted to initiate a rescue. Where the user has fallen yet has gotten up, is no longer in distress, or does not require emergency services, the user can then initiate sending of a "false alarm" to the other device for signaling to emergency services that the user is in fact not in need of their services. The emergency services can then cancel their rescue response. For example, false alarm component 314 can receive user input (e.g., via a button provided on motion sensor device 104) that indicates the user is not in distress. In response to such input, false alarm component can direct communication component 208 to send a 'false alarm' signal to the other device (e.g., remote device 106). Upon receipt of the 'false alarm' signal, the other device can initiate a protocol to notify emergency services that the previous request for help is no longer needed.

In other aspects, analysis component 308 can be configured to activate alarm component 312 as a secondary/alternative response when communication component 208 is unable to complete transmission of the distress signal to another device, wherein the other device is configured to activate emergency services based on receipt of the distress signal. For example, communication component 208 may be unable to complete transmission of the distress signal to another device where a wireless network required for transmission is unavailable or the other device is not properly paired with motion sensor device.

Analysis component 308 can employ various techniques to detect a falling motion of a user to which motion sensor device is attached based on collected motion data by sensor module 204. In an aspect, analysis component 308 can identify acceleration measurements that correspond to a free fall signal lasting over a threshold duration of time. For example, a free-fall signal for a person is represented by acceleration $(A)=-9.81\ ms^{-2}$. Where this free fall signal is in the direction towards ground (e.g., based on gravity) for more than 350 milliseconds, this indicates that a person is in the state of free-fall, for at least 1.0 meter. Similarly, if the signal lasts for about 1.0 second, that means a person is in the state of free-fall for about 5 meters. For the detection of falling, the falling signal should not last as long as a free fall signal. Therefore, one mechanism to detect falling includes identifying acceleration data that corresponds to an acceleration at or near the free fall acceleration of $(A)=-9.81\ ms^{-2}$ for a duration exceeding a threshold duration.

Analysis component 308 can further confirm that the user has in fact fallen and is in distress by observing motion following the falling signal data that corresponds to little or no movement by the user. For example, the user has fallen and cannot get up, little or no motion data will be generated by the sensor module. In an aspect, analysis component 308 can determine that a user has in fact fall and in distress when little or no motion data (e.g., a determined by motion data threshold) is received for a minimum duration of time (e.g., 30 seconds) following detection of a falling signal.

In another aspect, analysis component 308 can examine patterns in captured motion data that correspond to known movement patterns. For example, analysis component 308 can access stored information (e.g., in memory 306) identifying patterns (e.g., reference patterns) in motion data based on acceleration measurements, orientation measurements, direction measurements, velocity measurements, and/or distance measurements, for a human as function of time, that correspond to known movements. These known movements can include at least falling movements. For example, it is found that there are two types of falling, one is a linear fall and the other one is rotational fall. When acceleration data is graphically depicted against time, a linear fall is characterized by sharp spikes while a rotational fall is characterized by a wavelike pattern. In an aspect, analysis component 308 can compare captured motion data to known patterns corresponding to linear and rotational falling motions. In response to determination that the captured motion data matches or substantially matches a pattern for a linear or rotational fall, analysis component 308 can declare that a falling motion has been detected.

In addition to detection and characterization of falling motions, analysis component 308 can also identify other types of movement based on correspondence of patterns in captured motion data to reference patterns for known movements. For example, other identifiable movements can include but are not limited to: walking, running, jumping, rolling, walking stairs, and falling, standing up, laying or sitting down, etc., and any other movement by a person that can be distinguished by a pattern in the motion data (e.g., including minute movement such as specific gestures).

In an aspect, analysis component 308 can employ machine learning to techniques to match pattern in captured motion data to reference patterns that correspond to known types of motion. According to this aspect, analysis component 308 can employ inference component 310 to provide for or aid in various inferences or determinations associated with identifying and evaluating motion data. For example, inference component 310 can infer whether a falling motion is represented in captured motion data.

In order to provide for or aid in the numerous inferences described herein, inference component 310 can examine the entirety or a subset of the data to which it is granted access and can provide for reasoning about or infer states of the system, environment, etc. from a set of observations as captured via events and/or data. An inference can be employed to identify a specific context or action, or can generate a probability distribution over states, for example. The inference can be probabilistic—that is, the computation of a probability distribution over states of interest based on a consideration of data and events. An inference can also refer to techniques employed for composing higher-level events from a set of events and/or data.

Such an inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 4:
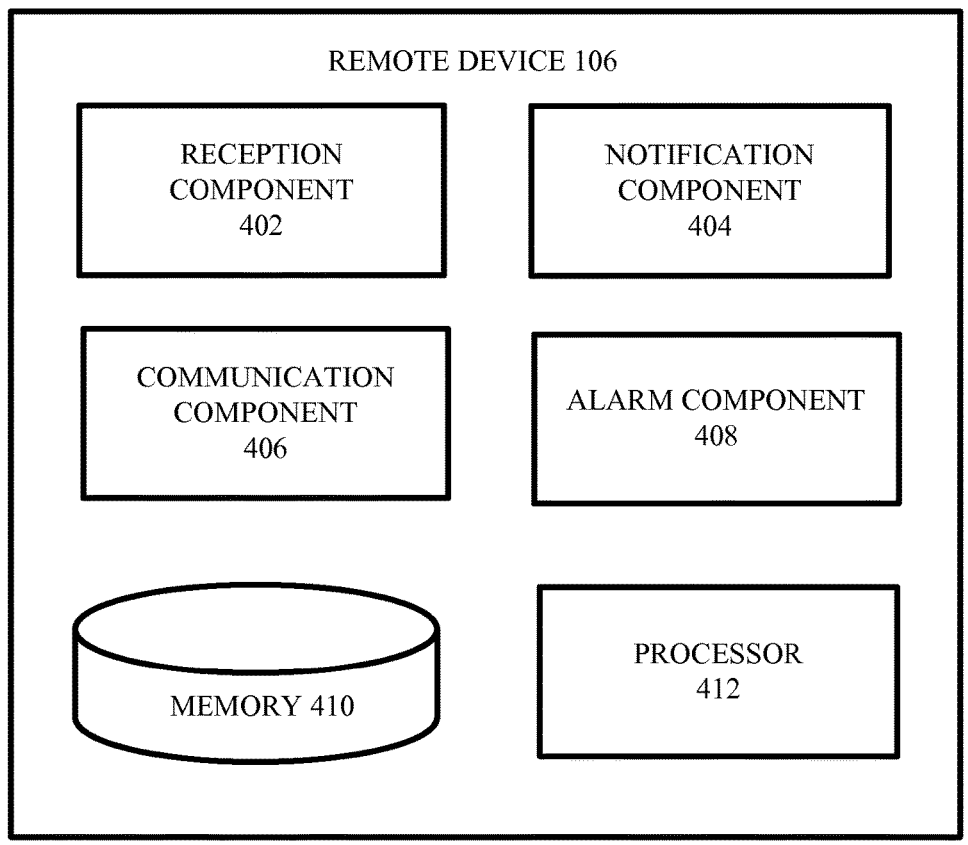
FIG. 4 presents an example remote device that facilitates notifying emergency services in response to detection of a user falling motion in accordance with various aspects and embodiments described herein.

FIG. 4 presents an exemplary embodiment of remote device 106 in accordance with aspects described herein. Repetitive description of like elements employed in respective embodiments of devices and systems described herein is omitted for sake of brevity.

Remote device 106 can function in various roles depending on the system architecture employed to accomplish processing of motion data captured by a motion sensor device 104 attached to another object or person. In one embodiment, remote device 106 can be configured to listen for distress and 'false alarm signals' emitted by a motion sensor device 104 with which it is paired and notify emergency service provider 100 based on receipt of such signals. According to this embodiment, remote device 402 can include reception component, notification component 404, communication component 406 and alarm component 408. Remote device 106 can further include memory 104 for storing computer executable components and instructions. Video segmentation platform 102 further includes a processor 102 to facilitate operation of the instructions (e.g., computer executable components and instructions) by video segmentation platform 102.

In an aspect, reception component 402 is configured to receive distress and 'false alarm' signals from a motion sensor device 104. For example, reception component 402 can be configured to listen for and identify distress and 'false alarm' signals emitted from a motion sensor device 104 with which it is paired. Reception component 402 can then inform notification component 404 when a distress or 'false alarm' signal has been received. In response to reception of a distress or signal, notification component 404 can activate a notification mechanism to notify another entity (e.g., emergency service provider 100) that the user wearing the motion senor device 104 has fallen and needs help. In an aspect, in association with the notification, remote device can include information that identifies, or facilitates identification of, the user identify and/or a location of the fallen user. The other entity or entities to which a notification is sent can be pre-configured by remote device 106. For example, the other entity or entities can include emergency service provider 100, a designated friend, a designated caregiver, and/or a nurse station in hospital or care facility, etc.

In an aspect, remote deice 106 can include a phone and the notification mechanism comprises initiation of a phone call to emergency services (or another designated entity). The notification mechanism can also activate a speaker function of the remote device 106 in association with the phone call so that the fallen user (who may not be able to access remote device 106) can speak with the phone call recipient and request help. In another example, notification component 404 can send an electronic message to the other entity (e.g., an email, a notification message, an SMS text message) notifying the other entity that the user has fallen and requesting help. Notification component 404 can employ a similar notification mechanism in response to receipt of a 'false alarm' signal. However the notification message sent to the other entity can indicate that the user is not in distress and does not need emergency services.

In an aspect, remote device 106 can also include an alarm component 408. Alarm component can employ similar functionality as alarm component 312. For example, in response to detection of a distress signal, alarm component 410 can sound an alarm that may be heard by nearby good Samaritans. In an aspect, alarm component 312 can employ this alarm function when remote communication component 406 cannot connect to a wireless network or another device.

Communication component 406 can facilitate wireless communication capabilities of remote device 106. For example, communication component 406 can establish a wireless PAN between remote device 406 and a motion sensor device via Bluetooth™, NFC, WiFi and the like. Communication component 406 can also facilitate connection of remote device 106 to a WAN (e.g., a cellular network, the Internet, and the like).

In another embodiment, remote device 106 can merely serve as a network node or access point device configured to relay (e.g., via communication component 406) raw or processed motion data received thereby (e.g., via reception component 402) from motion sensor device 104 to another system or device for processing thereof, such as motion analysis service provider 108 or emergency service provider 100. According to this aspect, motion analysis service provider 108 can provide remote (e.g., cloud based) motion based services in real-time or substantially real-time for a plurality of users or objects to which respective motion sensor devices are attached. Such motion analysis based services can include notification of emergency services in the event a detected fall. Other motion based services are discussed in greater detail with respect to FIG. 6.

Remote device 106 can include any suitable computing device configured to perform some or all of the functions described herein. For example, remote device 106 can include a desktop computer, a laptop computer, a television, an Internet enabled television, a mobile phone, a smartphone, a tablet personal computer (PC), or a personal digital assistant PDA. In an aspect, remote device 106 includes a phone or smartphone owned by the user wearing a motion sensor device 104. According to this aspect, the user can pair the user's phone to the user's motion sensor device 104.

Figure 5:
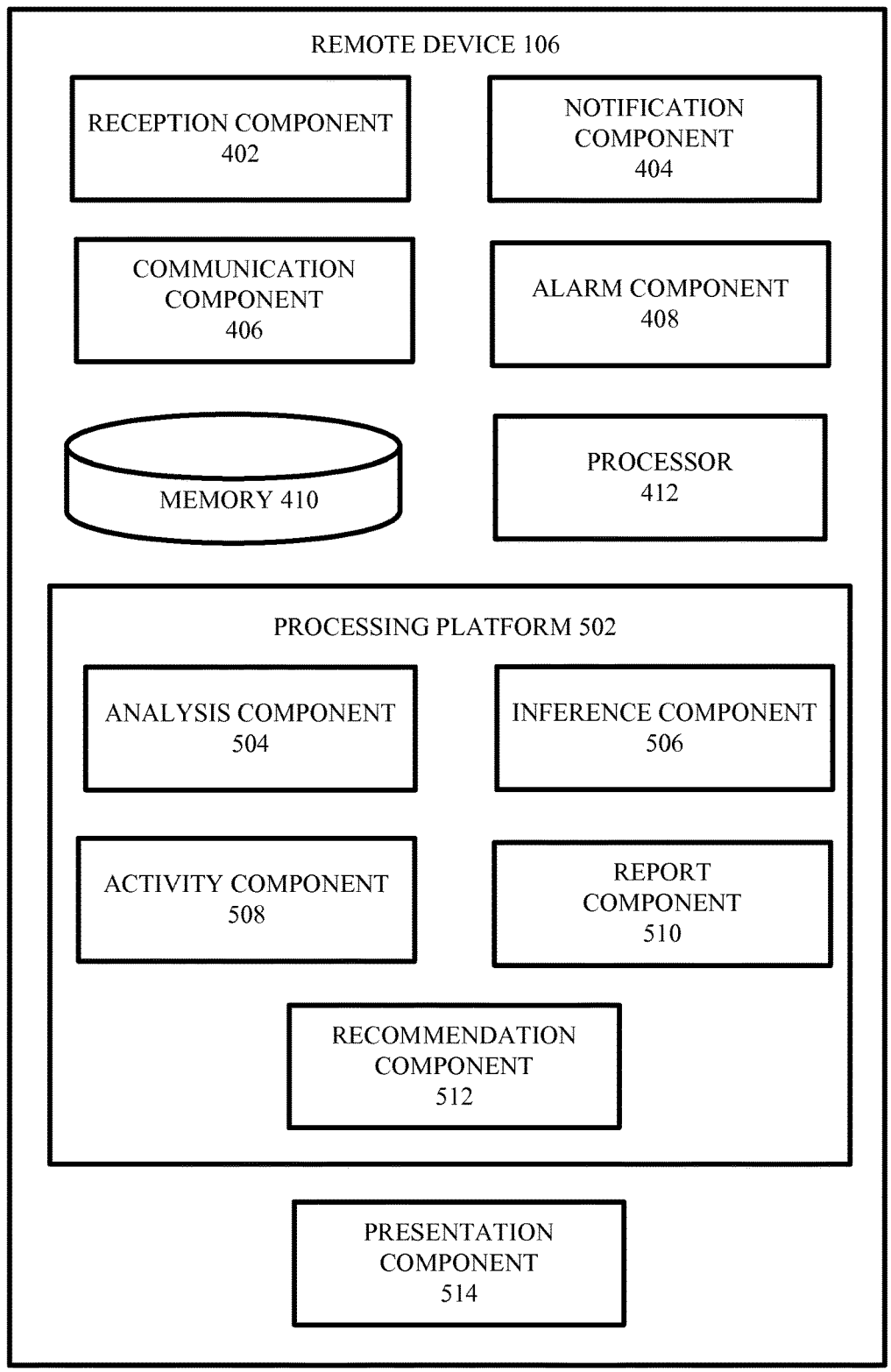
FIG. 5 presents another example remote device that facilitates notifying emergency services in response to detection of a user falling motion in accordance with various aspects and embodiments described herein.

FIG. 5 presents another exemplary embodiment of remote device 106 in accordance with aspects described herein. Repetitive description of like elements employed in respective embodiments of devices and systems described herein is omitted for sake of brevity.

As noted above, remote device 106 can function in various roles depending on the system architecture employed to accomplish processing of motion data captured by a motion sensor device 104 attached to another object or person. In accordance with another embodiment, remote device 106 can be configured to receive raw motion data captured by a motion sensor device 104 associated therewith, analyze/process the raw motion sensor data 104, and effectuate various responses (e.g., contacting emergency services) based on the analysis. According to this embodiment, remote device 106 can include processing platform 502 which includes analysis component 504, inference component 506, activity component 508, report component 510 and recommendation component 512.

In an aspect, analysis component 504 and inference component 506 can provide same or substantially similar functionality as analysis component 308 and inference component 310, respectively. For example, analysis component 504 can analyze received raw motion data in response to receipt of the raw motion data from a motion sensor device 104 (e.g., in real-time or substantially real-time) to identify a falling signal or a pattern in the motion data that correspond to a falling motion. Similar to inference component 310, inference component 506 can also employ machine learning techniques to infer when signals or patterns in raw motion data correlate to a information and/or a pattern corresponding to a falling motion.

Analysis component 504 and inference component 506 can further analyze motion data (or lack thereof), received immediately following the data corresponding to a falling motion to determine whether the fallen user gets up and recovers from the fall or whether the user cannot get up and needs help. For example, analysis component 504 can employ a time threshold for which to receive little or no motion data from the motion sensor 104 prior to notification of emergency services. For example, analysis component 504 can apply a rule wherein a fall is declared if after N seconds following the fall, little or no motion data is received. In response to detection of a falling motion, remote device 106 can employ notification component 404 to activate a notification mechanism as described supra with respect to notification component 40 and alarm component 408.

In addition to detection of user falling events, remote processing platform 502 can analyze raw motion data from various other angles to provide a variety of motion based services. For example, in addition to falling motions, analysis component 504 and inference component 506 can identify other motions included in received motion data for which known motion patterns can be determined and accessible to processing platform (e.g., in memory 410). For example, other motions can include but are not limited to: walking, running, jumping, rolling, walking stairs, and falling, standing up, laying or sitting down, etc. When definitive motions cannot be detected, analysis component 504 can employ received motion data to determine how active the user is, such as whether the user is exhibiting any movement and the intensity of the movement.

Activity component 508 can further analyze the various detected motions to provide feedback based on the motions. For example, activity component 508 can determine or infer user activity patterns over the course of a period of time (e.g., an hour, a day, a week, a month etc.) to identify patterns in the user's activity levels. These patterns can be correlated to health factors, such as calories burned, onset or recovery from an illness or physical ailment, sleep patterns, effect of various medications, etc. In an aspect, activity component 508 can provided real-time feedback. For example, as a user moves about the day, activity component 508 can provide information to the user regarding amount of calories burned, level of activity exhibited, amount of restful sleep obtained, how fast the user is moving, how high the user is jumping, etc.

In an aspect, activity component 508 can also analyze a specific activity and provide feedback regarding characteristics of the activity, including motion intensity levels at various points of the activity, acceleration/deceleration patterns of the activity, orientation, change of movements and various other characteristics of the activity. For example, a gymnast wearing a motion sensor device 104 at or near her waist while performing a vault on the vaulting apparatus could generate motion data regarding her running/sprinting approach to the spring board, her hurdle onto and off of the springboard, her hands touching and pushing off the vault, her body positions throughout the course of her off-flight trick (the off-flight may be as simple as leaping over the apparatus or as complicated as executing several twists and turns in the air), and her landing on the other side of the apparatus. Activity component 508 can analyze the various features and provide a comprehensive of characteristics of the gymnasts vault performance (e.g., how fast she runs on the approach, when she hurdles onto the springboard, when she dismounts from the vault, how high she flies, when she begins turning during her trick and how quickly she spins, etc.).

Report component 510 can generate reports with information generated by activity component 508. For example, report component 510 can generate a report that characterizes a users activity levels over the course of a week. The report can also compare the activity levels for that week against activity levels of other users or activity levels from a previous week. In another example, report component can generate a report that identifies changes in user activity levels over the course of recovery from injury. In another example, report component 510 can generate a report outlining characteristics of the gymnasts vault performance.

Recommendation component 512 is configured to provide recommendations to the user based on analysis performed by activity component 508 and prior collected data regarding user motions and activity performance as well as external information related to various standards (e.g., health standards, activity performance standards, etc.). For example, recommendation component 512 can determine or infer (e.g., using inference component 506) whether a user should increase or decrease the users activity level, whether the user should increase or decrease sleep, whether the user should jump higher, run faster, etc. Recommendation component 512 can then provide these recommendations to the user. In another example, regarding the gymnast's vault performance, recommendation component 512 can compare characteristics of the vault performance to prior vault performances of the user and/or known characteristics of a model vault performance to determine or infer how the user can improve. For example, recommendation component 512 can determine that the user should begin her double twist earlier. Recommendation component 512 can further provide these recommendations to the user.

Presentation component 514 is configured to generate a graphical user interface for displaying reports and other information processed by processing platform 502. This graphical user interface can facilitate user interaction with remote device 102 and the various features provided by processing platform 502. For example, presentation component 514 can present reports generated by report component 510. In another aspect, presentation component 514 can display graphical depictions of motion data received by remote device 106.

Figure 6:
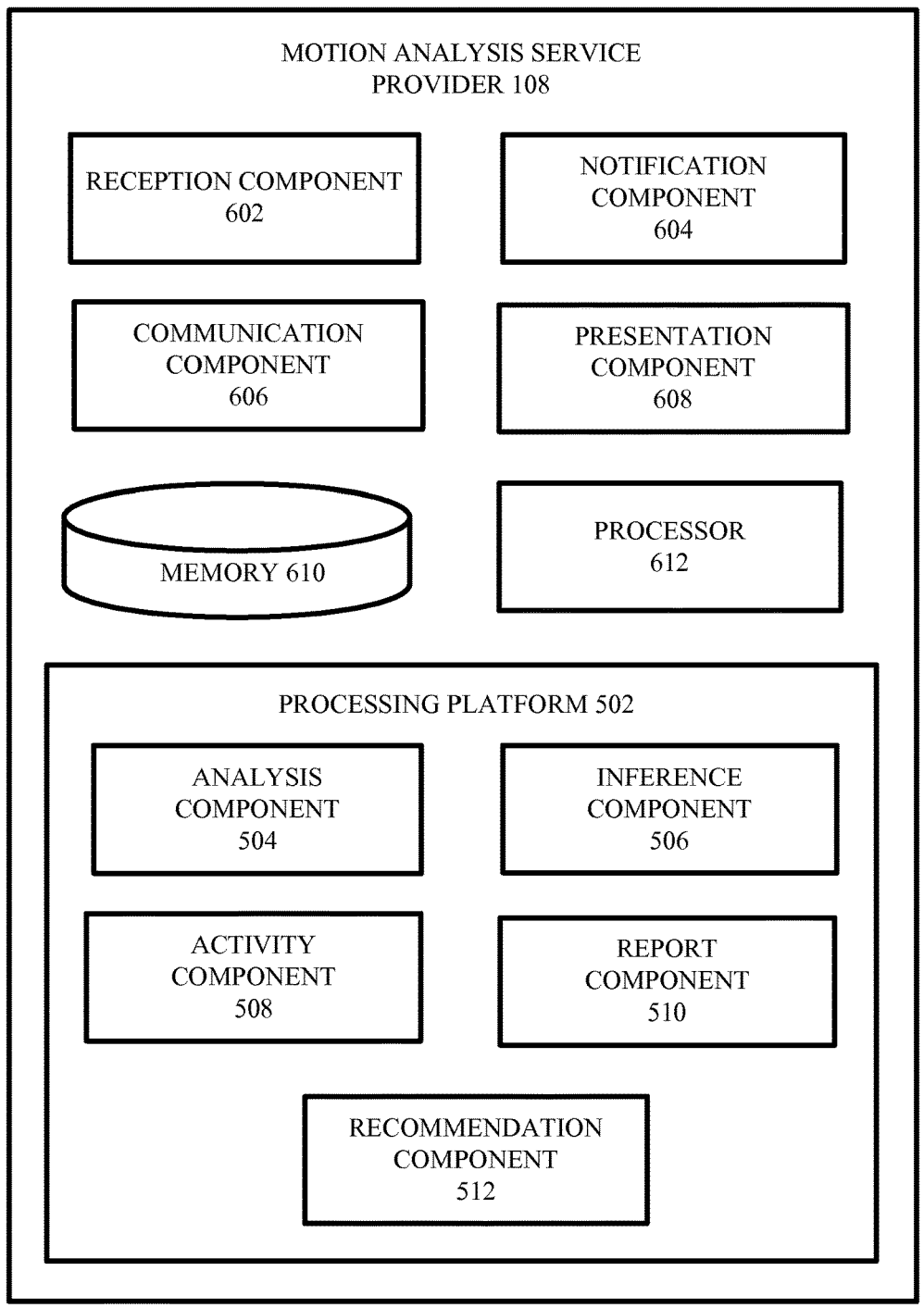
FIG. 6 presents an example motion analysis service provider that facilitates selecting monitoring and analyzing user motion in association with provision of various motion based services in accordance with various aspects and embodiments described herein.

FIG. 6 presents an exemplary embodiment of motion analysis service provider 108 in accordance with aspects described herein. Repetitive description of like elements employed in respective embodiments of devices and systems described herein is omitted for sake of brevity.

Motion analysis service provider 108 can include same or similar functionality as remote device 106, (particularly the embodiment described with respect to FIG. 5). For example, similar to the embodiment of remote device 106 discussed with respect to FIG. 5, motion analysis service provider 108 can include processing platform 502. Motion analysis service provider 108 can also include notification component 604, communication component 606, presentation component 608, memory 610 and processor 612. These components can respectively provide same or similar functionality as the corresponding components provided at remote device 106, discussed with respect to FIG. 5.

However, rather than providing motion based services for a single user paired to a particular motion sensor device 104, motion analysis service provider 108 can provide motion based services for a plurality of users wearing motion sensor devices 104. In essence, motion analysis service provider 108 can function as a cloud based server that receives and processes motion data to for a plurality of users to provide motion based services to the respective users. Motion analysis service provider 108 can receive the motion data via reception component 602 either directly from the respective motion sensor devices or indirectly via remote devices 106 (e.g., the users' mobile devices) paired with the respective motion sensor devices. Motion analysis service provider 108 can process the motion data in real-time to provide real-time motion based services (e.g., emergency services in response to falling detection, notifications when user should change activity levels, etc.) or non-real time to provide other services (e.g., a report analyzing a users sleep patterns or activity levels over a week period).

In an aspect, motion analysis service provider employs 108 a website platform that is accessed via users, such as wearers of motion sensor devices, using a client computing device, such as a remote device 106. For example, motion analysis service provider 108 can employ a website platform that allows users to access, view, and interact with various processing outputs (e.g., reports generated via report component 100) provided by processing platform 502 via a network (e.g., the Internet). In another aspect, motion analysis service provider 108 can function as a mobile application service provider. According to this aspect, motion analysis service provider can provide the motion based services afforded by processing platform 502 and notification component 604, as discussed herein, to mobile client devices via respective client applications provided at the mobile client devices.

In view of the example systems and/or devices described herein, example methods that can be implemented in accordance with the disclosed subject matter can be further appreciated with reference to flowcharts in FIGS. 7-10. For purposes of simplicity of explanation, example methods disclosed herein are presented and described as a series of acts; however, it is to be understood and appreciated that the disclosed subject matter is not limited by the order of acts, as some acts may occur in different orders and/or concurrently with other acts from that shown and described herein. For example, a method disclosed herein could alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a method in accordance with the subject specification. It should be further appreciated that the methods disclosed throughout the subject specification are capable of being stored on an article of manufacture to facilitate transporting and transferring such methods to computers for execution by a processor or for storage in a memory.

Figure 7:
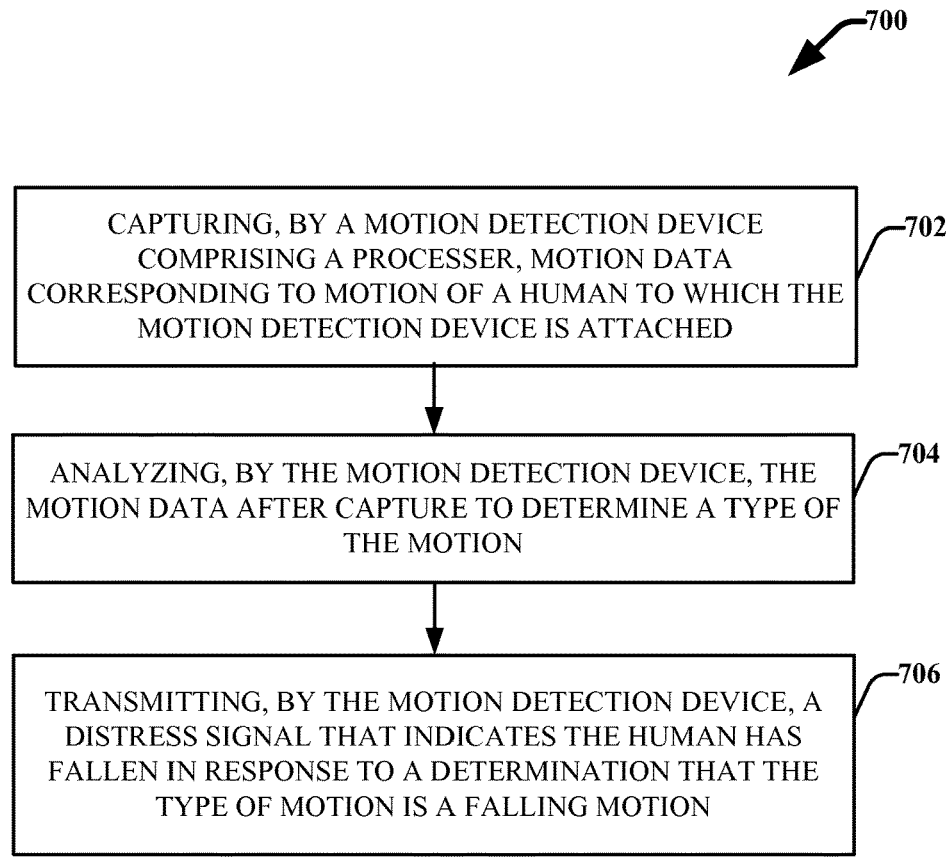
FIG. 7 is a flow diagram of an example method for capturing, monitoring and analyzing user motion to facilitate detecting when the user has fallen in accordance with aspects described herein.

FIG. 7 illustrates a flow chart of an example method 700 for capturing, monitoring and analyzing user motion to facilitate detecting when the user has fallen in accordance with aspects described herein. At 702, a motion detection device comprising a processor (e.g., motion sensor device 104) captures motion data corresponding to motion of a human to which the motion detection device is attached (e.g., via sensor module 204). At 704, the motion detection device determines a type of the motion (e.g., via analysis component 308). At 706, the motion detection device transmits a distress signal that indicates the human has fallen in response to a determination that the type of motion is a falling motion (e.g., via communication component 208).

Figure 8:
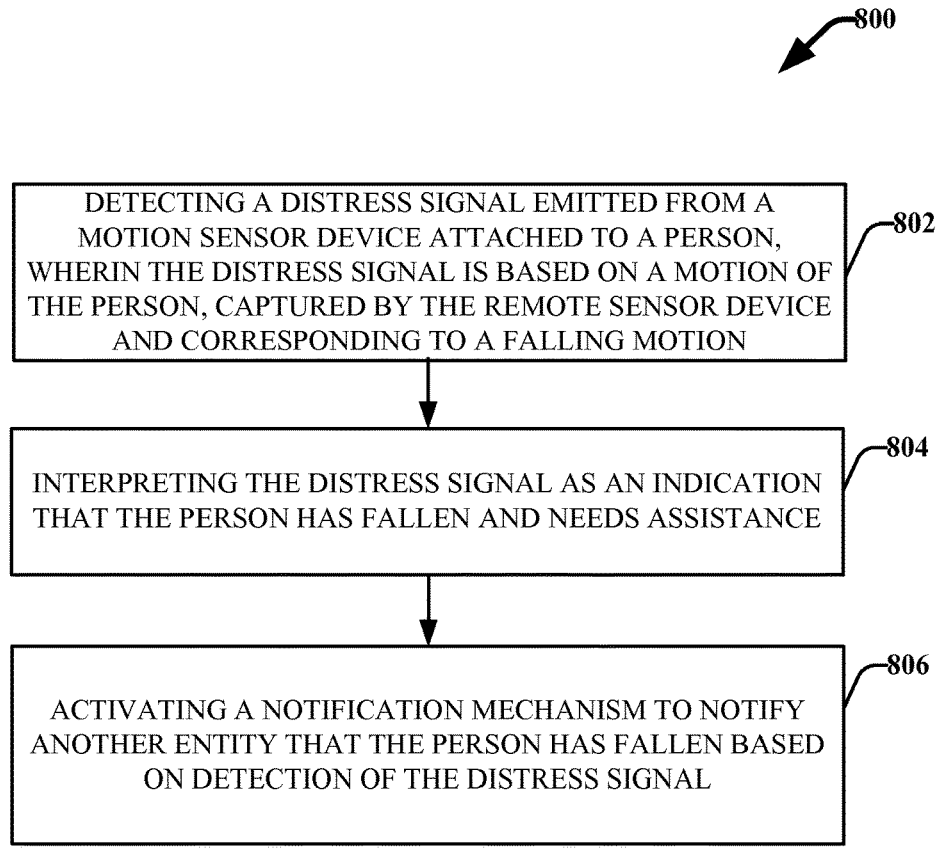
FIG. 8 is a flow diagram of another example method for capturing, monitoring and analyzing user motion to facilitate detecting when the user has fallen in accordance with aspects described herein.

FIG. 8 illustrates a flow chart of another example method 800 for capturing, monitoring and analyzing user motion to facilitate detecting when the user has fallen in accordance with aspects described herein. At 802, a distress signal emitted from a motion sensor device attached to a person (e.g., motion sensor device 104), is received (e.g., by reception component 402 or reception component 602). At 804, the distress signal is interpreted as an indication that the person has fallen. At 806, a notification mechanism is activated (e.g., via notification component 404 or notification component 604) to notify an entity (e.g., emergency service provider 100), that the person has fallen based on detection of the distress signal.

Figure 9:
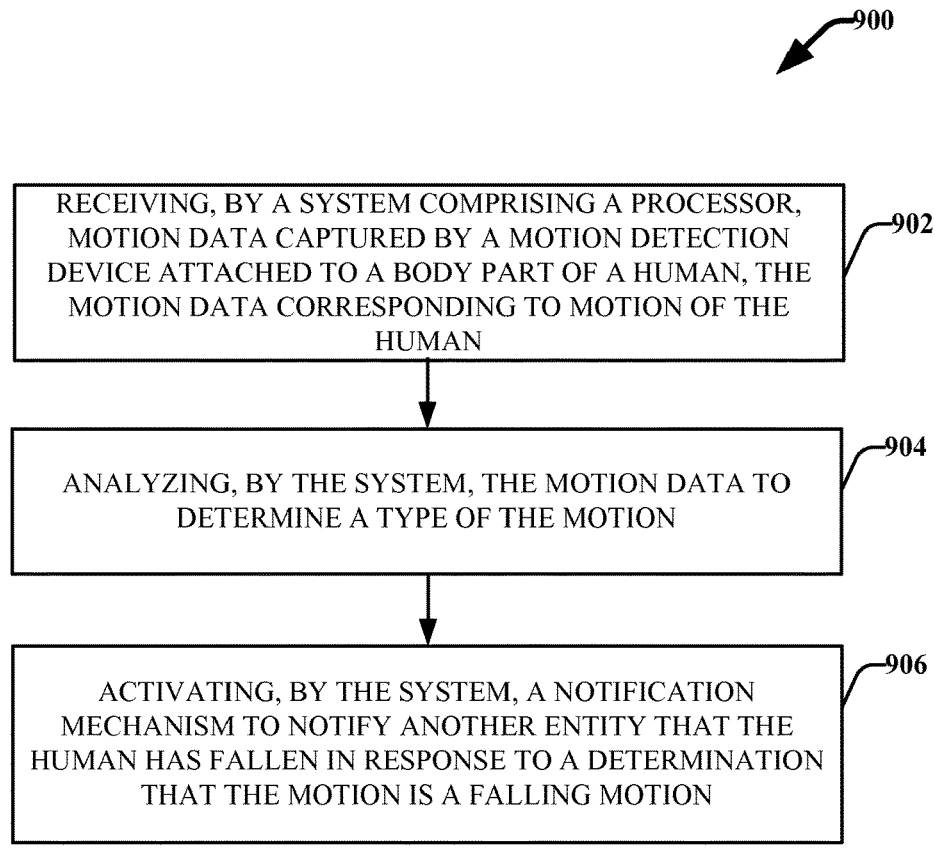
FIG. 9 is a flow diagram of another example method for capturing, monitoring and analyzing user motion to facilitate detecting when the user has fallen in accordance with aspects described herein.

FIG. 9 illustrates a flow chart of another example method 900 for capturing, monitoring and analyzing user motion to facilitate detecting when the user has fallen in accordance with aspects described herein. At 902, a system comprising a processor receives motion data captured by a motion detection device (e.g., device 104) attached to a body part of a human, the motion data corresponding to motion of the human (e.g., remote device 106 via reception component 402 or motion analysis service provider 108 via reception component 602). At 904, the system analyzes the motion data to determine a type of the motion (e.g., via analysis component 504). At 906, the system activates a notification mechanism to notify another entity that the human has fallen in response to a determination that the motion is a falling motion (e.g., using notification 404 or notification component 604).

Example Operating Environments

The systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

Figure 10:
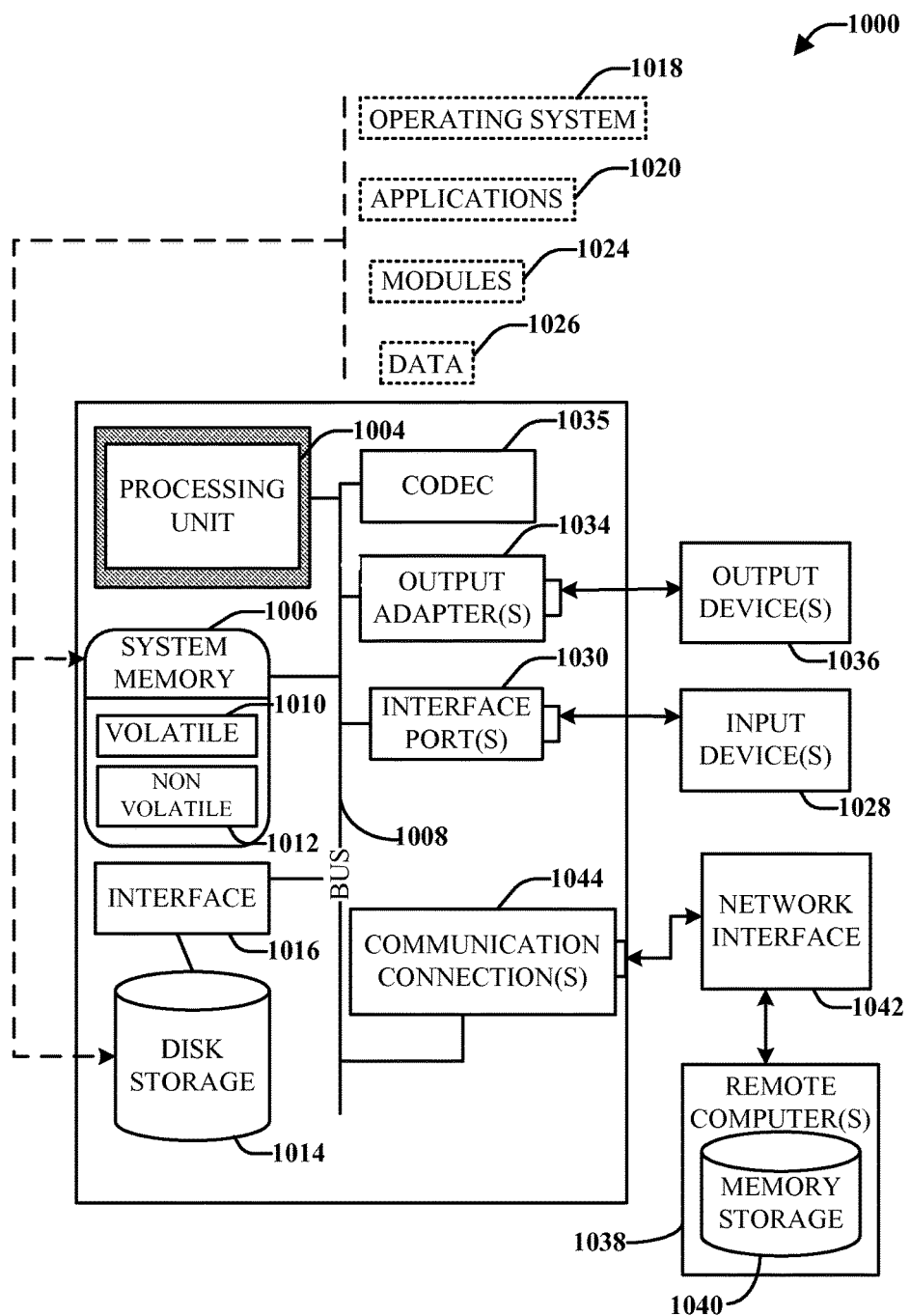
FIG. 10 is a schematic block diagram illustrating a suitable operating environment in accordance with various aspects and embodiments.

With reference to FIG. 10, a suitable environment 1000 for implementing various aspects of the claimed subject matter includes a computer 1002. The computer 1002 includes a processing unit 1004, a system memory 1006, a codec 1005, and a system bus 1008. The system bus 1008 couples system components including, but not limited to, the system memory 1006 to the processing unit 1004. The processing unit 1004 can be any of various available processors. Dual microprocessors and other multiprocessor architectures also can be employed as the processing unit 1004.

The system bus 1008 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire, and Small Computer Systems Interface (SCSI).

The system memory 1006 includes volatile memory 1010 and non-volatile memory 1012. The basic input/output system (BIOS), containing the basic routines to transfer information between elements within the computer 1002, such as during start-up, is stored in non-volatile memory 1012. In addition, according to present embodiments, codec 1005 may include at least one of an encoder or decoder, wherein the at least one of an encoder or decoder may consist of hardware, a combination of hardware and software, or software. Although, codec 1005 is depicted as a separate component, codec 1005 may be contained within non-volatile memory 1012. By way of illustration, and not limitation, non-volatile memory 1012 can include read only memory (ROM), programmable ROM (PROM), electrically programmable ROM (EPROM), electrically erasable programmable ROM (EEPROM), or flash memory. Volatile memory 1010 includes random access memory (RAM), which acts as external cache memory. According to present aspects, the volatile memory may store the write operation retry logic (not shown in FIG. 10) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ES-DRAM.

Computer 1002 may also include removable/non-removable, volatile/non-volatile computer storage medium. FIG. 10 illustrates, for example, disk storage 1014. Disk storage 1014 includes, but is not limited to, devices like a magnetic disk drive, solid state disk (SSD) floppy disk drive, tape drive, Jaz drive, Zip drive, LS-70 drive, flash memory card, or memory stick. In addition, disk storage 1014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1014 to the system bus 1008, a removable or non-removable interface is typically used, such as interface 1016.

It is to be appreciated that FIG. 10 describes software that acts as an intermediary between users and the basic computer resources described in the suitable operating environment 1000. Such software includes an operating system 1018. Operating system 1018, which can be stored on disk storage 1014, acts to control and allocate resources of the computer system 1002. Applications 1020 take advantage of the management of resources by operating system 1018 through program modules 1024, and program data 1026, such as the boot/shutdown transaction table and the like, stored either in system memory 1006 or on disk storage 1014. It is to be appreciated that the claimed subject matter can be implemented with various operating systems or combinations of operating systems.

A user enters commands or information into the computer 1002 through input device(s) 1028. Input devices 1028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1004 through the system bus 1008 via interface port(s) 1030. Interface port(s) 1030 include, for example, a serial port, a parallel port, a game port, and a universal serial bus (USB). Output device(s) 1036 use some of the same type of ports as input device(s). Thus, for example, a USB port may be used to provide input to computer 1002, and to output information from computer 1002 to an output device 1036. Output adapter 1034 is provided to illustrate that there are some output devices 1036 like monitors, speakers, and printers, among other output devices 1036, which require special adapters. The output adapters 1034 include, by way of illustration and not limitation, video and sound cards that provide a means of connection between the output device 1036 and the system bus 1008. It should be noted that other devices and/or systems of devices provide both input and output capabilities such as remote computer(s) 1038.

Computer 1002 can operate in a networked environment using logical connections to one or more remote computers, such as remote computer(s) 1038. The remote computer(s) 1038 can be a personal computer, a server, a router, a network PC, a workstation, a microprocessor based appliance, a peer device, a smart phone, a tablet, or other network node, and typically includes many of the elements described relative to computer 1002. For purposes of brevity, only a memory storage device 1040 is illustrated with remote computer(s) 1038. Remote computer(s) 1038 is logically connected to computer 1002 through a network interface 1042 and then connected via communication connection(s) 1044. Network interface 1042 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1044 refers to the hardware/software employed to connect the network interface 1042 to the bus 1008. While communication connection 1044 is shown for illustrative clarity inside computer 1002, it can also be external to computer 1002. The hardware/software necessary for connection to the network interface 1042 includes, for exemplary purposes only, internal and external technologies such as, modems including regular telephone grade modems, cable modems and DSL modems, ISDN adapters, and wired and wireless Ethernet cards, hubs, and routers.

Figure 11:
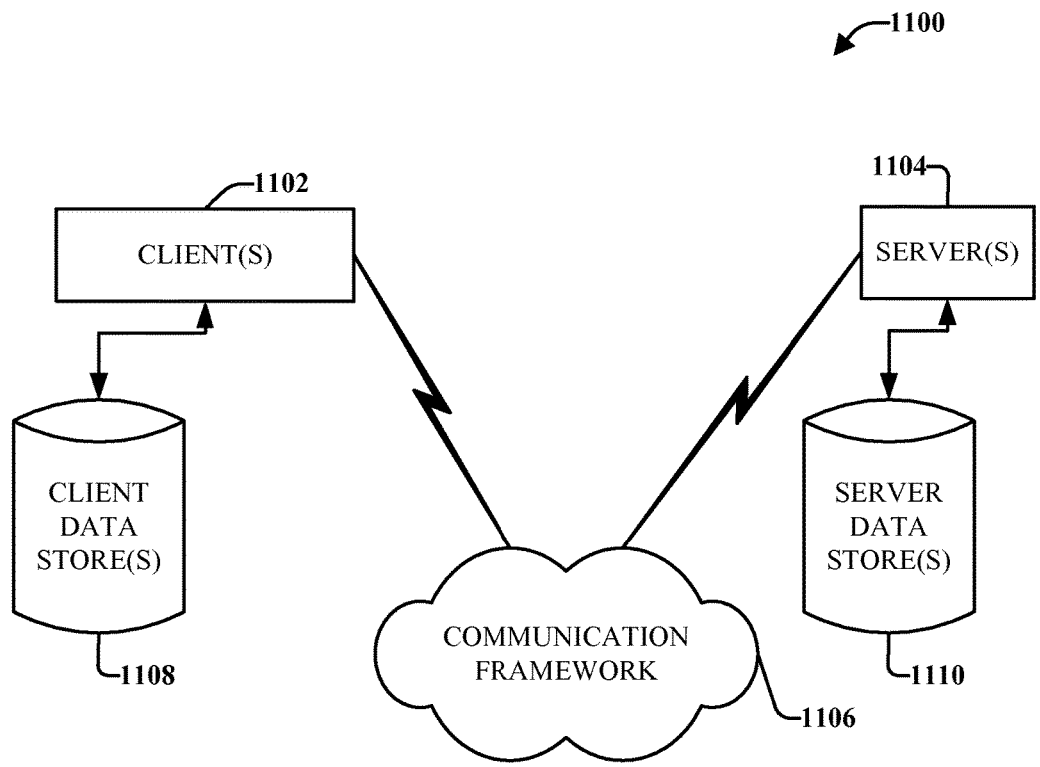
FIG. 11 is a schematic block diagram of a sample-computing environment in accordance with various aspects and embodiments.

Referring now to FIG. 11, there is illustrated a schematic block diagram of a computing environment 1100 in accordance with this disclosure. The system 1100 includes one or more client(s) 1102 (e.g., laptops, smart phones, PDAs, media players, computers, portable electronic devices, tablets, and the like). The client(s) 1102 can be hardware and/or software (e.g., threads, processes, computing devices). The system 1100 also includes one or more server(s) 1104. The server(s) 1104 can also be hardware or hardware in combination with software (e.g., threads, processes, computing devices). The servers 1104 can house threads to perform transformations by employing aspects of this disclosure, for example. One possible communication between a client 1102 and a server 1104 can be in the form of a data packet transmitted between two or more computer processes wherein the data packet may include video data. The data packet can include a metadata, e.g., associated contextual information, for example. The system 1100 includes a communication framework 1106 (e.g., a global communication network such as the Internet, or mobile network(s)) that can be employed to facilitate communications between the client(s) 1102 and the server(s) 1104.

Communications can be facilitated via a wired (including optical fiber) and/or wireless technology. The client(s) 1102 include or are operatively connected to one or more client data store(s) 1108 that can be employed to store information local to the client(s) 1102 (e.g., associated contextual information). Similarly, the server(s) 1104 are operatively include or are operatively connected to one or more server data store(s) 1110 that can be employed to store information local to the servers 1104.

In one embodiment, a client 1102 can transfer an encoded file, in accordance with the disclosed subject matter, to server 1104. Server 1104 can store the file, decode the file, or transmit the file to another client 1102. It is to be appreciated, that a client 1102 can also transfer uncompressed file to a server 1104 and server 1104 can compress the file in accordance with the disclosed subject matter. Likewise, server 1104 can encode video information and transmit the information via communication framework 1106 to one or more clients 1102.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement one or more of the various embodiments. Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject embodiments are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the various embodiments can include a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject embodiments may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from any computer-readable device or storage media.

What is claimed is:

1. A device, comprising:
   a housing that attaches to a body part of a human;
   a speaker;
   a sensor module comprising an accelerometer and a gyroscope that capture motion data corresponding to motions of the human to which the device is attached, wherein the motion data comprises acceleration data captured by the accelerometer and rotational data captured by the gyroscope, and wherein the sensor module captures the motion data over samplings periods that are controlled by an external device;
   a memory that stores executable components; and
   a processor that executes or facilitates execution of the executable components, the executable components comprising:
      a communication component that facilitates establishment of a wireless communication link between the device and the external device, wherein based on the establishment of the wireless communication link and the capture of the motion data, the communication component sends the motion data to the external device via the wireless communication link, and wherein the external device is configured to process the motion data to determine whether a falling motion is detected;
a storage component that stores the motion data at the device in response to an inability of the device to establish the wireless communication link with the external device and a first determination that a sampling rate at which the motion data is captured is classified as being a high sampling rate, resulting in stored motion data;
an analysis component that analyzes the stored motion data to determine characteristics of the motions; and
an alarm component that activates an alarm of the device based on a second determination that the characteristics indicate the falling motion.

2. The device of claim 1, wherein the sensor module captures the motion data corresponding to at least one of: the falling motion, a walking motion, a running motion, a climbing motion, or a jumping motion.

3. The device of claim 1, wherein the sensor module comprises an inertial measurement unit.

4. The device of claim 1, wherein the acceleration data indicates acceleration of the device as a function of time, and wherein the analysis component determines that the characteristics indicate the falling motion based on the acceleration data comprising a free fall signal over a duration of the time that exceeds a threshold duration.

5. The device of claim 1, wherein the analysis component determines the characteristics indicate the falling motion based on identification of a pattern in the acceleration data and the rotational data that corresponds to a falling motion pattern.

6. The device of claim 5, wherein the analysis component employs a machine learning technique to match the pattern in the acceleration data and the rotational data to a reference pattern that corresponds to the falling motion pattern.

7. The device of claim 1, wherein the analysis component is further configured to determine defined types of movements performed by the human over the sampling periods based on the characteristics.

8. The device of claim 7, wherein the analysis component is further configured to determine information regarding intensity of the defined types of movements and duration of the defined types of movements over the sampling periods based on the characteristics.

9. The device of claim 8, wherein based on the defined types of movements and the information regarding the intensity and duration of the defined types of movements, the analysis component is configured to determine sleep information regarding sleep patterns of the human.

10. The device of claim 8, wherein based on the defined types of movements and the information regarding the intensity and duration of the defined types of movements, the analysis component is configured to determine activity information regarding activity patterns of the human.

11. The device of claim 10, wherein the computer executable components further comprise:
a report component configured to generate a report regarding the activity information for the human relative to additional activity information regarding activity levels of other humans.

12. The device of claim 7, wherein the analysis component is configured to employ machine learning to determine the defined types of movements.

13. A device, comprising:
a speaker;
a memory that stores executable components; and
a processor that executes or facilitates execution of the executable components, comprising:
a control component configured to control capture of motion data by a motion detection device at defined sampling periods, wherein the motion detection device is attached to a body part of a human, and wherein the motion data comprises acceleration data captured by an accelerometer of the motion detection device and rotational data captured by a gyroscope of the motion detection device;
a reception component configured to receive the motion data from the motion detection device, wherein the device is remote from the motion detection device;
a communication component configured to facilitate establishment of a wireless communication link between the device and a remote server device, wherein based on the establishment of the wireless communication link and reception of the motion data, the communication component sends the motion data to the remote server device via the wireless communication link, and wherein remote server device is configured to process the motion data to determine whether a falling motion is detected;
a storage component that stores the motion data at the device, resulting in stored motion data, wherein the storage component stores the motion data at the device in response to an inability of the device to establish the wireless communication link with the remote server device or a first determination that a sampling rate at which the motion data is captured is classified as a high sampling rate;
an analysis component that analyzes the stored motion data to determine patterns in the motion data; and
an alarm component that activates an alarm of the device in response to a second determination that a pattern of the patterns corresponds to a falling motion.

14. The device of claim 13, wherein the external device is further configured to send an electronic message to emergency services that indicates the human has fallen in response to detection of the falling motion.

15. The device of claim 13, wherein the analysis component is configured to determine that the pattern corresponds to the falling motion based on the acceleration data comprising a free fall signal over a first duration of time exceeding a threshold duration followed by an inactivity signal over a second duration of time exceeding a minimum duration.

16. The device of claim 13, wherein the analysis component is configured to employ a machine learning technique to match the pattern to a defined falling motion pattern.

17. The device of claim 13, wherein the alarm comprises an audible sound emitted via the speaker.

18. A method, comprising:
controlling, by a device comprising a processor, capture of motion data by a motion detection device at defined sampling periods, wherein the motion detection device is attached to a body part of a human, and wherein the motion data comprises acceleration data captured by an accelerometer of the motion detection device and rotational data captured by a gyroscope of the motion detection device;
receiving, by the device, the motion data from the motion detection device in response to the capture of the motion data by the motion detection device, wherein the device is remote from the motion sensing device;

initiating, by the device, establishment of a wireless communication link between the device and a remote server device based on the receiving the motion data;

based on the establishment of the wireless communication link, sending, by the device, the motion data to the remote server device via the wireless communication link to enable processing by the remote server device to determine whether the motion data indicates a falling motion has occurred;

storing the motion data by the device, resulting in stored motion data, wherein the storing comprises storing the motion data in response to a failure of the establishment of the wireless communication link or a first determination that a sampling rate at which the motion data is captured is classified as a high sampling rate;

analyzing, by the device, the stored motion data to determine characteristics of motions of the human; and activating, by the device, an alarm of the device based on a second determination that the characteristics indicate the falling motion.

19. The method of claim 18, wherein the remote server device is configured to send an electronic message to emergency services that indicates the human has fallen in response to determining the falling motion has occurred.

20. The method of claim 18, wherein the analyzing comprises determining that the characteristics indicate the falling motion based on the acceleration data comprising a free fall signal over a duration of time exceeding a threshold duration.

21. A device, comprising:
a housing that attaches to a body part of a human;
a transmitter;
a speaker;
an inertial measurement unit that captures motion data corresponding to motions of the human to which the device is attached, wherein the motion data comprises acceleration data and rotational data, and wherein the inertial measurement unit captures the motion data over sampling periods that are controlled by an external device;
a memory that stores executable components; and
a processor that executes or facilitates execution of the executable components, the executable components comprising:

a communication component that activates the transmitter and employs the transmitter to transmit the motion data to the external device in response to the motion data being captured, wherein the external device is configured to process the motion data to determine whether a falling motion has occurred;

a storage component that stores the motion data at the device, resulting in stored motion data, wherein the storage component stores the motion data at the device in response to at least one of:
the transmitter being unable to complete the transmission of the motion data to the external device, and
a determination that a sampling rate at which the motion data is captured is classified as a high sampling rate.

22. The device of claim 21, wherein the motion data further comprises tilting data and velocity data.

23. The device of claim 21, wherein the executable components further comprise:
an analysis component that analyzes the stored motion data to determine characteristics of the motions.

24. The device of claim 23, wherein the executable components further comprise:
an activity component that determines activity information regarding patterns in activity levels of the human based on the characteristics of the motions.

25. The device of claim 24, wherein activity information comprises calorie information regarding an amount of calories burned by the human.

26. The device of claim 24, wherein activity information comprises sleep information regarding sleep patterns of the human.

27. The device of claim 24, wherein the motion data is captured in association with performance of an activity by the human, and the executable components further comprise:
a recommendation component that employs one or more classifiers and artificial intelligence to determine a modification to an aspect of the performance of the activity and generates recommendation information identifying the modification.

* * * * *